United States Patent
Yamamoto et al.

(10) Patent No.: US 11,589,753 B2
(45) Date of Patent: Feb. 28, 2023

(54) ACOUSTIC WAVE DEVICE AND CONTROL METHOD OF ACOUSTIC WAVE DEVICE

(71) Applicant: FUJIFILM Corporation, Tokyo (JP)

(72) Inventors: Katsuya Yamamoto, Kanagawa (JP); Tomoki Inoue, Kanagawa (JP); Keiji Tsubota, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 111 days.

(21) Appl. No.: 16/923,817

(22) Filed: Jul. 8, 2020

(65) Prior Publication Data

US 2020/0337561 A1   Oct. 29, 2020

Related U.S. Application Data

(63) Continuation of application No. PCT/JP2018/045315, filed on Dec. 10, 2018.

(30) Foreign Application Priority Data

Jan. 31, 2018 (JP) .............................. JP2018-015279

(51) Int. Cl.
*A61B 5/00* (2006.01)

(52) U.S. Cl.
CPC .......... *A61B 5/0095* (2013.01); *A61B 5/6848* (2013.01); *A61B 5/7425* (2013.01)

(58) Field of Classification Search
CPC .... A61B 5/0095; A61B 5/6848; A61B 5/7425
(Continued)

(56) References Cited

U.S. PATENT DOCUMENTS

2004/0002643 A1* 1/2004 Hastings ................ A61B 5/062
  600/407
2006/0264743 A1* 11/2006 Kleen ................ A61B 5/02007
  600/431
(Continued)

FOREIGN PATENT DOCUMENTS

JP   2015-043969 A   3/2015
JP   2016-036643 A   3/2016
(Continued)

OTHER PUBLICATIONS

International Search Report issued in PCT/JP2018/045315; dated Feb. 12, 2019.
(Continued)

*Primary Examiner* — Amelie R Davis
*Assistant Examiner* — John Denny Ll
(74) *Attorney, Agent, or Firm* — Studebaker & Brackett PC

(57) ABSTRACT

An acoustic wave device includes an insertion object having a photoacoustic wave generator, a light source that irradiates the photoacoustic wave generator with light, an insertion object image signal generator that generates an insertion object image signal from a photoacoustic wave reception signal from the photoacoustic wave generator, and an insertion object display image signal generator that generates an insertion object display image signal having a center at a peak position where a signal strength of the insertion object image signal becomes a peak value, having a maximum width corresponding to a predetermined reference signal width, and having a signal strength corresponding to the peak value at the center.

20 Claims, 20 Drawing Sheets

(58) Field of Classification Search
USPC .......................................................... 600/407
See application file for complete search history.

(56) References Cited

U.S. PATENT DOCUMENTS

| | | | |
|---|---|---|---|
| 2009/0326556 A1* | 12/2009 | Diolaiti | A61B 1/00087 |
| | | | 606/130 |
| 2015/0161802 A1* | 6/2015 | Christiansen | A61B 90/94 |
| | | | 348/74 |
| 2016/0135689 A1* | 5/2016 | Murakoshi | A61B 5/0095 |
| | | | 600/407 |
| 2018/0008369 A1* | 1/2018 | Murakoshi | A61B 3/10 |
| 2019/0090962 A1* | 3/2019 | Boettner | A61B 34/20 |
| 2020/0242769 A1* | 7/2020 | Limburg | H04N 17/002 |

FOREIGN PATENT DOCUMENTS

| | | | |
|---|---|---|---|
| JP | 2016-064011 A | 4/2016 | |
| WO | WO-2016158060 A1 * | 10/2016 | ............. A61B 90/35 |

OTHER PUBLICATIONS

International Preliminary Report on Patentability and Written Opinion issued in PCT/JP2018/045315; dated Aug. 4, 2020.

\* cited by examiner

ACOUSTIC WAVE DEVICE AND CONTROL METHOD OF ACOUSTIC WAVE DEVICE

CROSS-REFERENCE TO RELATED APPLICATIONS

This application is a Continuation of PCT International Application No. PCT/JP2018/045315 filed on Dec. 10, 2018, which claims priority under 35 U.S.C § 119(a) to Japanese Patent Application No. 2018-015279 filed on Jan. 31, 2018. Each of the above application(s) is hereby expressly incorporated by reference, in its entirety, into the present application.

BACKGROUND OF THE INVENTION

1. Field of the Invention

The present invention relates to an acoustic wave device and a control method of the acoustic wave device, and more particularly, to an acoustic wave device including an insertion object such as a puncture needle and a control method of the acoustic wave device.

2. Description of the Related Art

In the related art, a technique for obtaining a tomographic image of a subject using acoustic waves such as ultrasonic waves and photoacoustic waves is known. For example, an ultrasonic wave device that obtains a tomographic image of a subject using ultrasonic waves generally transmits an ultrasonic beam from an array transducer in which a plurality of elements are arranged toward the inside of the subject, and receives ultrasonic echoes from the subject using the array transducer to acquire element data. Further, the ultrasonic wave device may electrically process the acquired element data to generate an ultrasonic image in which a portion of the subject is included. Further, for example, a photoacoustic wave device that obtains a tomographic image of a subject using photoacoustic waves generally irradiates the inside of the subject with laser beam emitted from a laser light source, and receives photoacoustic waves emitted from an in-vivo substance such as hemoglobin included in a tissue of the subject using an array transducer to acquire element data. The photoacoustic wave device may electrically process the element data to generate a photoacoustic image in which a portion of the subject is included.

Further, in the related art, a technique for performing treatments such as sampling and injection of a drug solution by inserting an insertion object such as a puncture needle into a subject has been used. In a case where the treatments such as the sampling and the injection of the drug solution are performed using the insertion object in this way, for safety of the subject, various measures capable of confirming a position of a distal end portion of the insertion object have been devised.

For example, JP2016-064011A discloses an ultrasonic wave device that is provided with a puncture needle having a photoacoustic wave generator at a distal end portion thereof, irradiates the photoacoustic wave generator with laser beam, and receives generated photoacoustic waves to generate an image of the distal end portion of the puncture needle. The ultrasonic wave device disclosed in JP2016-064011A displays a composite image in which the image of the distal end portion of the puncture needle is superimposed on a tomographic image of the subject generated using ultrasonic waves on a display.

SUMMARY OF THE INVENTION

However, according to reviews of the present inventors, for example, in a case where an insertion object such as a puncture needle having a photoacoustic wave generator at a distal end portion thereof, as disclosed in JP2016-064011A, is inserted into a blood vessel, there is a concern that a so-called artifact may occur in which an image of the distal end portion of the insertion object is expanded and displayed. In such a case, there is a problem in that a user cannot easily recognize a tissue or the like included in a tomographic image of a subject due to the presence of the artifact, and thus, it is difficult for the user to confirm an accurate position of the distal end portion of the insertion object.

The present invention has been made in order to solve such a related-art problem, and an object of the present invention is to provide an acoustic wave device and a control method of the acoustic wave device capable of preventing a situation where a tissue or the like of a subject included in an acoustic wave image is not easily visually recognized by a user due to the presence of an artifact.

In order to achieve the above object, according to an aspect of the present invention, there is provided an acoustic wave device including: a subject beam irradiator that irradiates an inside of a subject with an ultrasonic beam or laser beam to cause an acoustic wave to be emitted from a tissue of the subject; an insertion object that is able to be inserted into the subject and has a photoacoustic wave generator at a distal end portion thereof; an insertion object laser light source that generates a photoacoustic wave from the photoacoustic wave generator by irradiating the photoacoustic wave generator of the insertion object with laser beam; and a reception signal generator that receives the acoustic wave emitted from the tissue of the subject to generate a tomographic image generating reception signal, and receives the photoacoustic wave from the photoacoustic wave generator to generate an insertion object image generating reception signal; a tomographic image signal generator that generates a tomographic image signal that represents a tomographic image of the subject from the tomographic image generating reception signal; an insertion object image signal generator that generates an insertion object image signal that represents an image of the distal end portion of the insertion object from the insertion object image generating reception signal; an insertion object display image signal generator that generates an insertion object display image signal having a center at a peak position where a signal strength of the insertion object image signal becomes a peak value, having a maximum width corresponding to a predetermined reference signal width, and having a signal strength corresponding to the peak value at the center; and a display, in which the acoustic wave device superimposes the tomographic image of the subject and the image of the distal end portion of the insertion object to be displayed on the display on the basis of the tomographic image signal and the insertion object display image signal.

Further, the acoustic wave device may further include a first signal width detector that detects a first signal width of the insertion object image signal having a signal strength of a predetermined ratio to the peak value, in which the insertion object display image signal generator may generate, in a case where the first signal width is larger than the reference signal width, an insertion object display image signal formed by a portion ranging from the center to the reference signal width in the insertion object image signal, and may generate, in a case where the first signal width is smaller than the reference signal width, an insertion object display image signal having a signal strength greater than a predetermined lower limit signal strength in all portions thereof, from the insertion object image signal.

Further, the insertion object display image signal generator may generate, in a case where the first signal width is smaller than the reference signal width, the insertion object display image signal obtained by increasing a signal strength of a portion including the signal strength smaller than the lower limit signal strength, in the insertion object image signal, up to the lower limit signal strength.

Alternatively, the insertion object display image signal generator may generate, in a case where the first signal width is smaller than the reference signal width, the insertion object display image signal obtained by enlarging a signal width of a portion including a signal strength larger than the lower limit signal strength, in the insertion object image signal, up to the reference signal width.

In addition, the acoustic wave device may further include an image highlighting unit that highlights the image of the distal end portion of the insertion object to be displayed on the display.

The image highlighting unit may superimpose an outline of a region having a center at the peak position and having the first signal width and the image of the distal end portion of the insertion object to be displayed on the display.

Further, the image highlighting unit may display an outer peripheral portion of the image of the distal end portion of the insertion object in different colors on the display between a case where the first signal width is larger than the reference signal width and a case where the first signal width is smaller than the reference signal width.

Further, the image highlighting unit may display the image of the distal end portion of the insertion object in different colors on the display between a case where the first signal width is larger than the reference signal width and a case where the first signal width is smaller than the reference signal width.

The acoustic wave device may further include: an operating unit through which a user performs an input operation; and a reference signal width setting unit that sets the reference signal width, in which the reference signal width setting unit may set a value set by the user through the operating unit as the reference signal width.

Alternatively, the acoustic wave device may further include: a reference signal width setting unit that sets the reference signal width; and a distal end diameter recording unit that records a diameter of the distal end portion of the insertion object, in which the reference signal width setting unit may calculate a converted value obtained by multiplying the diameter of the distal end portion of the insertion object recorded in the distal end diameter recording unit by a predetermined coefficient, and may set the converted value as the reference signal width.

The subject beam irradiator may irradiate the inside of the subject with an ultrasonic beam to cause an ultrasonic echo to be emitted from the tissue of the subject, and the reception signal generator may receive the ultrasonic echo from the tissue of the subject to generate the tomographic image generating reception signal.

Alternatively, the subject beam irradiator may irradiate the inside of the subject with laser beam to cause a photoacoustic wave to be emitted from the tissue of the subject, and the reception signal generator may receive the photoacoustic wave from the tissue of the subject to generate the tomographic image generating reception signal.

According to another aspect of the present invention, there is provided a control method of an acoustic wave device, the method including: receiving an acoustic wave emitted from a tissue of a subject by irradiating the inside of the subject with an ultrasonic beam or laser beam to generate a tomographic image generating reception signal; irradiating a photoacoustic wave generator of an insertion object with laser light, the insertion object being able to be inserted into the subject and having the photoacoustic wave generator at a distal end portion; receiving a photoacoustic wave from the photoacoustic wave generator to generate an insertion object image generating reception signal; generating an insertion object image signal that represents an image of the distal end portion of the insertion object from the insertion object image generating reception signal; generating a tomographic image signal that represents a tomographic image of the subject from the tomographic image generating reception signal; generating an insertion object display image signal having a center at a peak position where a signal strength of the insertion object image signal becomes a peak value, having a maximum width corresponding to a predetermined reference signal width, and having a signal strength corresponding to the peak value at the center; and superimposing the tomographic image of the subject and the image of the distal end portion of the insertion object to be displayed on a display on the basis of the tomographic image signal and the insertion object display image signal.

According to the present invention, since there are provided there is provided an insertion object image signal generator that generates an insertion object image signal that represents an image of a distal end portion of the insertion object from the insertion object image generating reception signal; and an insertion object display image signal generator that generates an insertion object display image signal having a center at a peak position where a signal strength of the insertion object image signal becomes a peak value, having a maximum width corresponding to a predetermined reference signal width, and having a signal strength corresponding to the peak value at the center, it is possible to prevent a situation where an acoustic wave image is not easily visually recognized due to the presence of an artifact.

DESCRIPTION OF THE PREFERRED EMBODIMENTS

Hereinafter, embodiments of the present invention will be described with reference to the accompanying drawings.

First Embodiment

Figure 1:
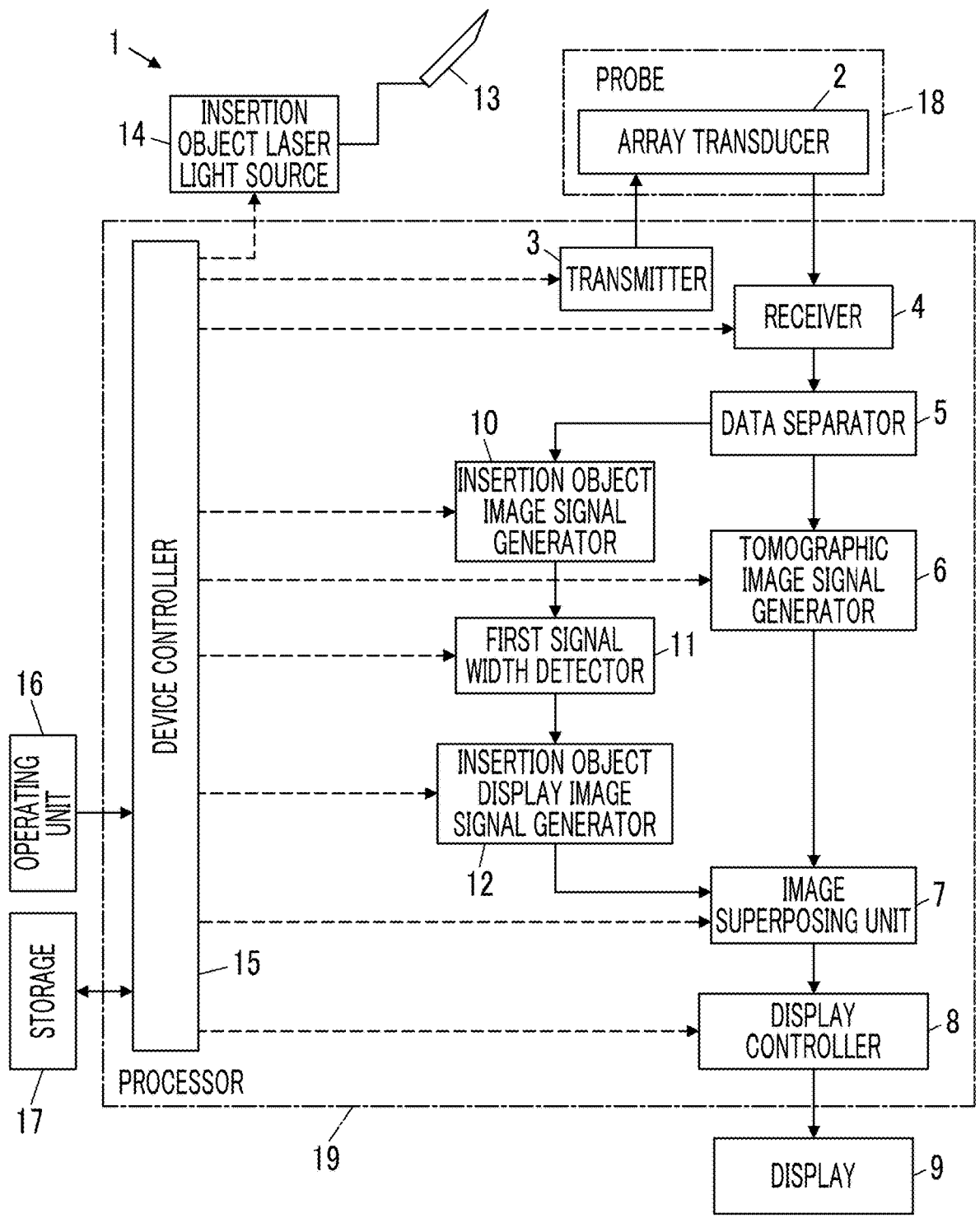
FIG. 1 is a block diagram showing a configuration of an ultrasonic wave device according to a first embodiment of the present invention.

FIG. 1 shows a configuration of an ultrasonic wave device 1 that is an acoustic wave device according to a first embodiment of the present invention. As shown in FIG. 1, the ultrasonic wave device 1 includes an array transducer 2, and a transmitter 3 and a receiver 4 are respectively connected to the array transducer 2. A data separator 5, a tomographic image signal generator 6, an image superposing unit 7, a display controller 8, and a display 9 are sequentially connected to the receiver 4. Further, an insertion object image signal generator 10 is connected to the data separator 5. Further, a first signal width detector 11 and an insertion object display image signal generator 12 are sequentially connected to the insertion object image signal generator 10. Further, the insertion object display image signal generator 12 is connected to the image superposing unit 7. In addition, the ultrasonic wave device 1 includes an insertion object 13, and the insertion object 13 is connected to an insertion object laser light source 14.

Further, a device controller 15 is connected to the transmitter 3, the receiver 4, the tomographic image signal generator 6, the image superposing unit 7, the display controller 8, the insertion object image signal generator 10, the first signal width detector 11, the insertion object display image signal generator 12, and the insertion object laser light source 14, and an operating unit 16 and a storage 17 are connected to the device controller 15. The device controller 15 and the storage 17 are connected to each other so that bidirectional information exchange can be performed.

In addition, the array transducer 2 is included in a probe 18, and a processor 19 is configured by the transmitter 3, the receiver 4, the data separator 5, the tomographic image signal generator 6, the image superposing unit 7, the display controller 8, the insertion object image signal generator 10, the first signal width detector 11, the insertion object display image signal generator 12, and the device controller 15.

Figure 2:
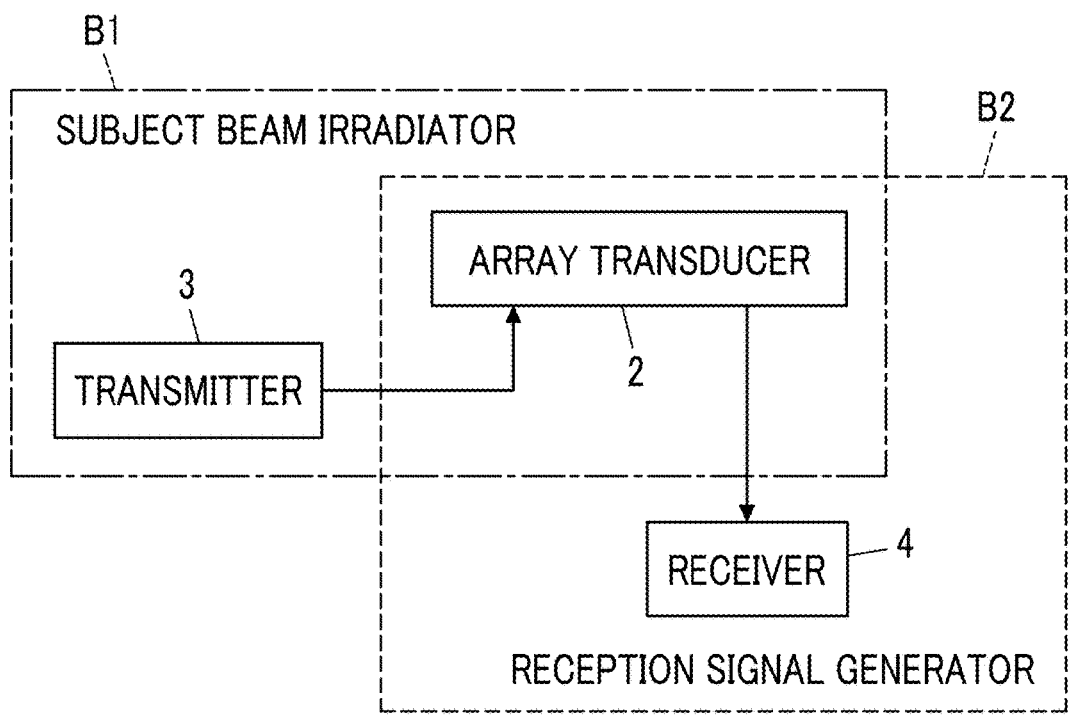
FIG. 2 is a block diagram showing an internal configuration of a subject beam irradiator and a reception signal generator according to the first embodiment of the present invention.

As shown in FIG. 2, a subject beam irradiator B1 is configured by the array transducer 2 and the transmitter 3, and a reception signal generator B2 is configured by the array transducer 2 and the receiver 4.

Figure 3:
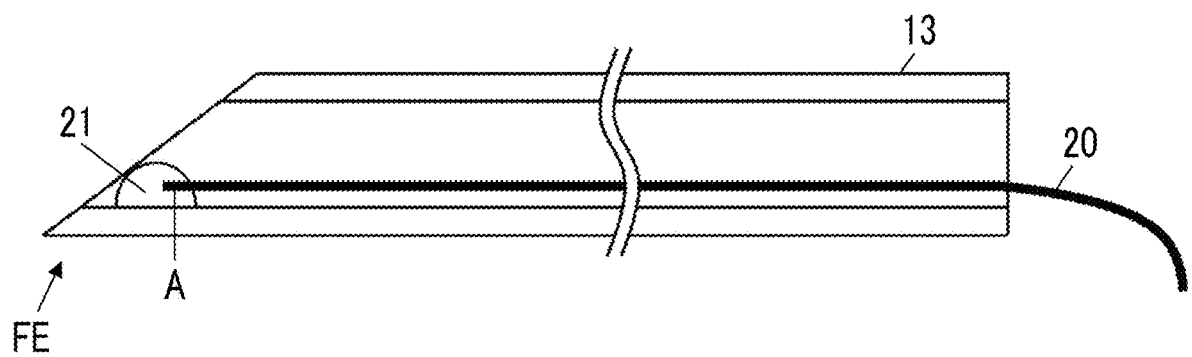
FIG. 3 is a diagram showing an example of an insertion object according to the first embodiment of the present invention.

An insertion object 13 shown in FIG. 1 is inserted into a subject in a case where ultrasonic diagnosis is performed, and is used for performing treatments such as sampling and injection of a drug solution. As the insertion object 13, for example, a puncture needle, a catheter, forceps, or the like may be used, but a puncture needle as shown in FIG. 3 may be used, for example. Inside the insertion object 13 shown in FIG. 3, a light guide member 20 such as an optical fiber is provided so as to extend from the insertion object laser light source 14 disposed outside to the vicinity of a distal end portion FE of the insertion object 13. Further, inside the insertion object 13, a photoacoustic wave generator 21 is disposed in the vicinity of the distal end portion FE of the insertion object 13, and a distal end portion A of the light guide member 20 is embedded in the photoacoustic wave generator 21.

The photoacoustic wave generator 21 is made of a material that absorbs light, for example, a synthetic resin such as an epoxy resin, a fluorine resin, or a polyurethane resin mixed with a black pigment, and contracts and expands according to irradiation of light to generate photoacoustic waves. In the insertion object 13 shown in FIG. 3, as light emitted from the insertion object laser light source 14 is applied to the photoacoustic wave generator 21 via the light guide member 20, photoacoustic waves are generated from the photoacoustic wave generator 21.

Figure 4:
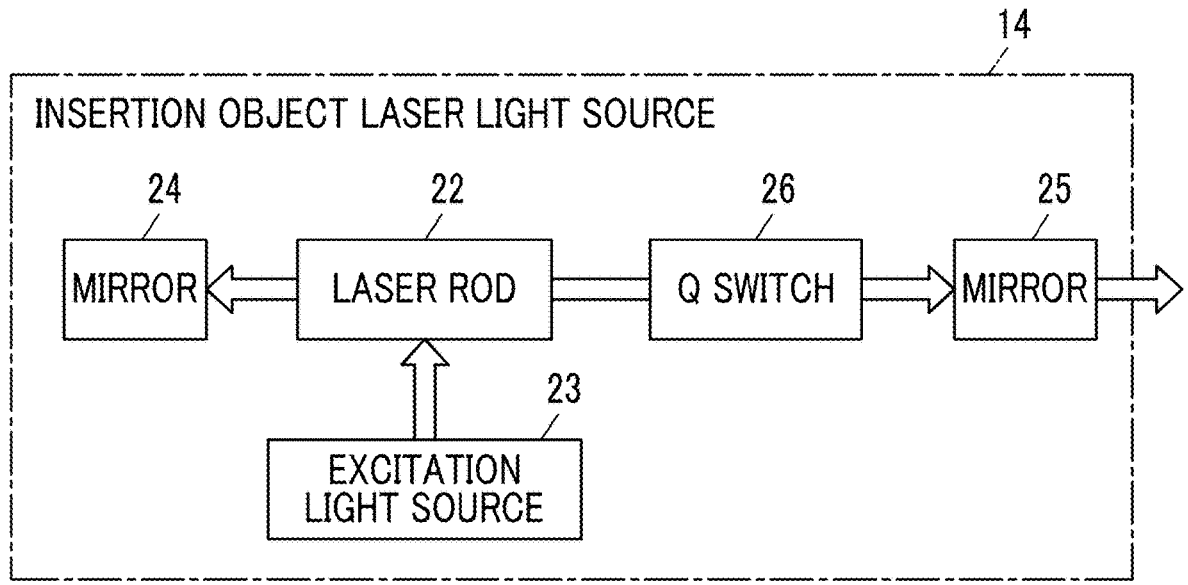
FIG. 4 is a block diagram showing an internal configuration of an insertion object laser light source according to the first embodiment of the present invention.

The insertion object laser light source 14 includes a laser rod 22, an excitation light source 23, a mirror 24, a mirror 25, and a Q switch 26, as shown in FIG. 4. The laser rod 22 is a laser medium, and for example, an alexandrite crystal may be used as the laser rod 22. The excitation light source 23 is a light source that irradiates the laser rod 22 with excitation light, and for example, a light source such as a flash lamp and a laser diode may be used as the excitation light source 23.

The mirrors 24 and 25 face each other with the laser rod 22 being interposed therebetween, and the mirrors 24 and 25 form an optical resonator. In this optical resonator, the mirror 25 is disposed on the output side. The Q switch 26 is inserted in the optical resonator, in which the Q switch 26 rapidly changes the state of the optical resonator from a state where an insertion loss is large to a state where the insertion loss is small, to thereby make it possible to obtain pulsed laser beam. The pulsed laser beam emitted from the mirror 25 on the output side of the insertion object laser light source 14 is guided to the insertion object 13 through the light guide member 20.

The array transducer 2 of the probe 18 shown in FIG. 1 has a plurality of transducers arranged one-dimensionally or two-dimensionally. Each of these transducers transmits an ultrasonic wave in accordance with a drive signal supplied from the transmitter 3, receives an ultrasonic echo from a subject, and outputs a tomographic image generating reception signal. Further, these elements receive a photoacoustic wave generated by irradiating the photoacoustic wave generator 21 of the insertion object 13 with light from the insertion object laser light source 14, and output an insertion object image generating reception signal.

Each transducer is formed by forming electrodes at both ends of a piezoelectric body made of, for example, a piezoelectric ceramic represented by lead zirconate titanate (PZT), a polymer piezoelectric element represented by polyvinylidene fluoride (PVDF: poly vinylidene di fluoride), a piezoelectric single crystal represented by lead magnesium niobate-lead titanate (PMN-PT: solid solution of lead magnesium niobate-lead titanate), or the like.

The transmitter 3 of the processor 19 includes, for example, a plurality of pulse generators, and supplies each drive signal to the plurality of transducers with an adjusted delay so that the ultrasonic waves transmitted from the plurality of transducers of the array transducer 2 form an ultrasonic beam on the basis of a transmission delay pattern selected according to a control signal from the device controller 15. As described above, in a case where a pulsed voltage or a continuous wave voltage is applied to the electrodes of the transducer of the array transducer 2, the piezoelectric body expands and contracts, and a pulsed ultrasonic wave or a continuous ultrasonic wave is generated from each transducer, and an ultrasonic beam is formed from a composite wave of such ultrasonic waves.

The transmitted ultrasonic beam is reflected by a target such as a portion of a subject, and propagates toward the array transducer 2 of the probe 18. The ultrasonic echo that propagates toward the array transducer 2 is received by each transducer that forms the array transducer 2. Here, each transducer that forms the array transducer 2 expands and contracts according to the reception of the propagating ultrasonic echo to generate an electric signal, and output the electric signal to the receiver 4 as a tomographic image generating reception signal.

Further, the photoacoustic wave generated by irradiating the photoacoustic wave generator 21 of the insertion object 13 with light emitted from the insertion object laser light source 14 is also received by each transducer that forms the array transducer 2. Here, each transducer that forms the array transducer 2 expands and contracts according to the reception of the photoacoustic wave, in a similar way to the reception of the ultrasonic wave, to generate an electric signal, and outputs the electric signal to the receiver 4 as an insertion object image generating reception signal.

Figure 5:
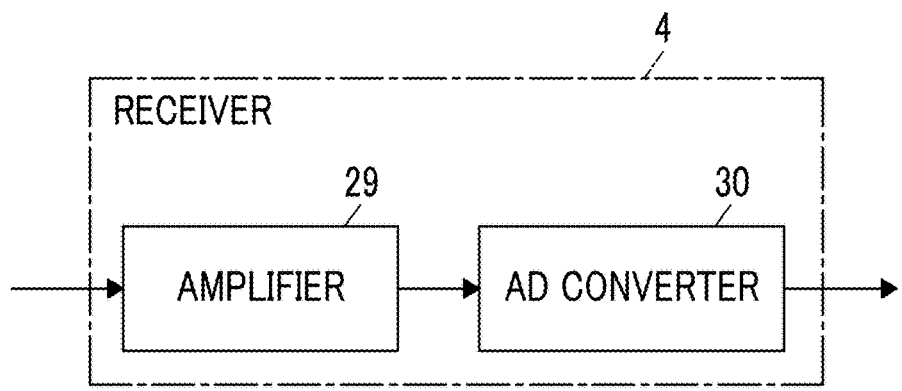
FIG. 5 is a block diagram showing an internal configuration of a receiver according to the first embodiment of the present invention.

The receiver 4 of the processor 19 processes the tomographic image generating reception signal and the insertion object image generating reception signal output from the array transducer 2 according to a control signal from the device controller 15. As shown in FIG. 5, the receiver 4 has a configuration in which an amplifier 29 and an analog digital (AD) converter 30 are connected in series. The amplifier 29 amplifies the tomographic image generating reception signal and the insertion object image generating reception signal input from each of the elements that form the array transducer 2, and transmits the amplified reception signals to the AD converter 30. The AD converter 30 converts the tomographic image generating reception signal and the insertion object image generating reception signal transmitted from the amplifier 29 into digitized data, respectively, and transmits the data to the data separator 5 of the processor 19.

The data separator 5 of the processor 19 separates the data of the tomographic image generating reception signal output from the receiver 4 from the data of the insertion object image generating reception signal, outputs the data of the tomographic image generating reception signal to the tomographic image signal generator 6, and outputs the data of the insertion object image generating reception signal to the insertion object image signal generator 10.

Figure 6:
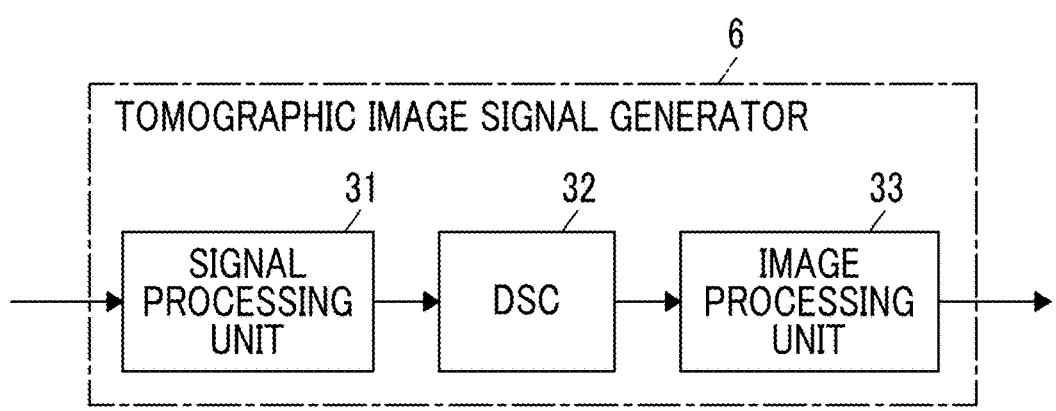
FIG. 6 is a block diagram showing an internal configuration of a tomographic image signal generator according to the first embodiment of the present invention.

As shown in FIG. 6, the tomographic image signal generator 6 of the processor 19 has a configuration in which a signal processing unit 31, a digital scan converter (DSC) 32, and an image processing unit 33 are connected in series. The signal processing unit 31 performs a reception focus process of giving each delay to each piece of data of the tomographic image generating reception signal on the basis of a reception delay pattern selected according to a control signal from the device controller 15 and performing addition (phasing addition). By the reception focus process, a sound ray signal in which a focus of an ultrasonic echo is narrowed to one scan line is generated. In addition, the signal processing unit 31 corrects attenuation due to a propagation distance according to the depth of a position where an ultrasonic wave is reflected for the generated sound ray signal, and then, performs an envelope detection process to generate a B-mode image signal that is tomographic image information on a tissue inside the subject. The B-mode image signal generated in this way is output to the DSC 32.

The DSC 32 of the tomographic image signal generator 6 raster-converts the B-mode image signal into an image signal according to a normal television signal scanning method. The image processing unit 33 of the tomographic image signal generator 6 performs a variety of necessary image processing such as brightness correction, gradation correction, sharpness correction, and color correction for the image data obtained by the DSC 32, and then, outputs the B-mode image signal to the image superposing unit 7.

The insertion object image signal generator 10 of the processor 19 generates an insertion object image signal that represents an image of the distal end portion FE of the insertion object 13 from the insertion object image generating reception signal. Although not shown, the insertion object image signal generator 10 has the same internal configuration as in the tomographic image signal generator 6. In a case where an insertion object image generating reception signal is input from the data separator 5 to the insertion object image signal generator 10, the insertion object image signal generator 10 performs the same process as the process performed by the tomographic image signal generator 6 for the insertion object image generating reception signal, and generates an insertion object image signal that represents an image of the distal end portion FE of the insertion object 13.

The first signal width detector 11 of the processor 19 detects a first signal width of an insertion object image signal having a signal strength of a predetermined ratio to a peak value of a signal strength in the insertion object image signal generated by the insertion object image signal generator 10. The first signal width refers to the width of a signal group having the signal strength of the predetermined ratio to the peak value of the signal strength in the insertion object image signal generated by the insertion object image signal generator 10. For example, in a case where the predetermined ratio is set to 20%, the first signal width detector 11 detects a signal width of an insertion object image signal having a value of 20% of the peak value of the signal strength of the insertion object image signal, as the first signal width.

However, in a case where the distal end portion FE of the insertion object 13 is inserted into a blood vessel or the like, a photoacoustic wave that propagates around the distal end portion FE of the insertion object 13 may not be easily attenuated. Accordingly, for example, in a case where the distal end portion FE of the insertion object 13 is inserted into the blood vessel, an insertion object image signal having a high signal strength may be obtained in a wide range centering around the peak value, compared with a typical insertion object image signal in a case where the distal end portion FE of the insertion object 13 is not inserted into the blood vessel, for example. In a case where such an insertion object image signal is displayed on the display 9, a so-called artifact is generated in which the image of the distal end portion FE of the insertion object 13 is displayed in an expanded state. The insertion object display image signal generator 12 of the processor 19 generates an insertion object display image signal adjusted so that a signal width of the insertion object image signal becomes a maximum width corresponding to a predetermined reference signal width in order to prevent such an artifact from being displayed on the display 9.

Here, the insertion object display image signal generator 12 generates the insertion object display image signal on the basis of the first signal width of the insertion object image signal detected by the first signal width detector 11 and the predetermined reference signal width.

Here, the reference signal width is a signal width set as a display width of the image of the distal end portion FE of the insertion object 13. It is preferable that the reference signal width is set so that a tomographic image of a subject on which the image of the distal end portion FE of the insertion object 13 is superimposed is visually recognized and the image of the distal end portion FE of the insertion object 13 is sufficiently clearly visually recognized by a user.

The image superposing unit 7 of the processor 19 superimposes the tomographic image of the subject and the image of the distal end portion FE of the insertion object 13 on the basis of the tomographic image signal generated by the tomographic image signal generator 6 and the insertion object display image signal generated by the insertion object display image signal generator 12, and outputs the result to the display controller 8. Here, the "superimposition of the tomographic image of the subject and the image of the distal end portion FE of the insertion object 13" means simple superimposition of the tomographic image of the subject generated on the basis of the tomographic image signal and the image of the distal end portion FE of the insertion object 13 generated on the basis of the insertion object display image signal, or generation of one image in which the tomographic image of the subject and the image of the distal end portion FE of the insertion object 13 are superimposed by forming a composite signal obtained by combining the tomographic image signal and the insertion object display image signal.

The device controller 15 of the processor 19 controls each unit of the ultrasonic wave device 1 on the basis of a program stored in advance in the storage 17 or the like and a user operation through the operating unit 16.

The display controller 8 of the processor 19 performs predetermined processing for an image output from the image superposing unit 7 under the control of the device controller 15 to generate an image that can be displayed on the display 9.

The display 9 of the ultrasonic wave device 1 displays an image generated by the display controller 8, and includes a display device such as a liquid crystal display (LCD).

The operating unit 16 of the ultrasonic wave device 1 is a unit through which a user performs an input operation, and may be configured to include a keyboard, a mouse, a trackball, a touch pad, a touch panel, and the like.

The storage 17 stores an operation program and the like of the ultrasonic wave device 1. The storage 17 may be configured by a recording medium such as a hard disc drive (HDD), a solid state drive (SSD), a flexible disc (FD), a magneto-optical (MO) disc, a magnetic (MT) tape, a random access memory (RAM), a compact disc (CD), a digital versatile disc (DVD), a secure digital (SD) card or a universal serial bus (USB) memory, a server connected to a network, or the like.

The processor 19 including the transmitter 3, the receiver 4, the data separator 5, the tomographic image signal generator 6, the image superposing unit 7, the display controller 8, the insertion object image signal generator 10, the first signal width detector 11, the insertion object display image signal generator 12, and the device controller 15 may be configured by a central processing unit (CPU), and a control program for causing the CPU to execute various processes, but may be configured using a digital circuit. Further, the transmitter 3, the receiver 4, the data separator 5, the tomographic image signal generator 6, the image superposing unit 7, the display controller 8, the insertion object image signal generator 10, the first signal width detector 11, the insertion object display image signal generator 12, and the device controller 15 may be partially or wholly integrated into one CPU.

Figure 7:
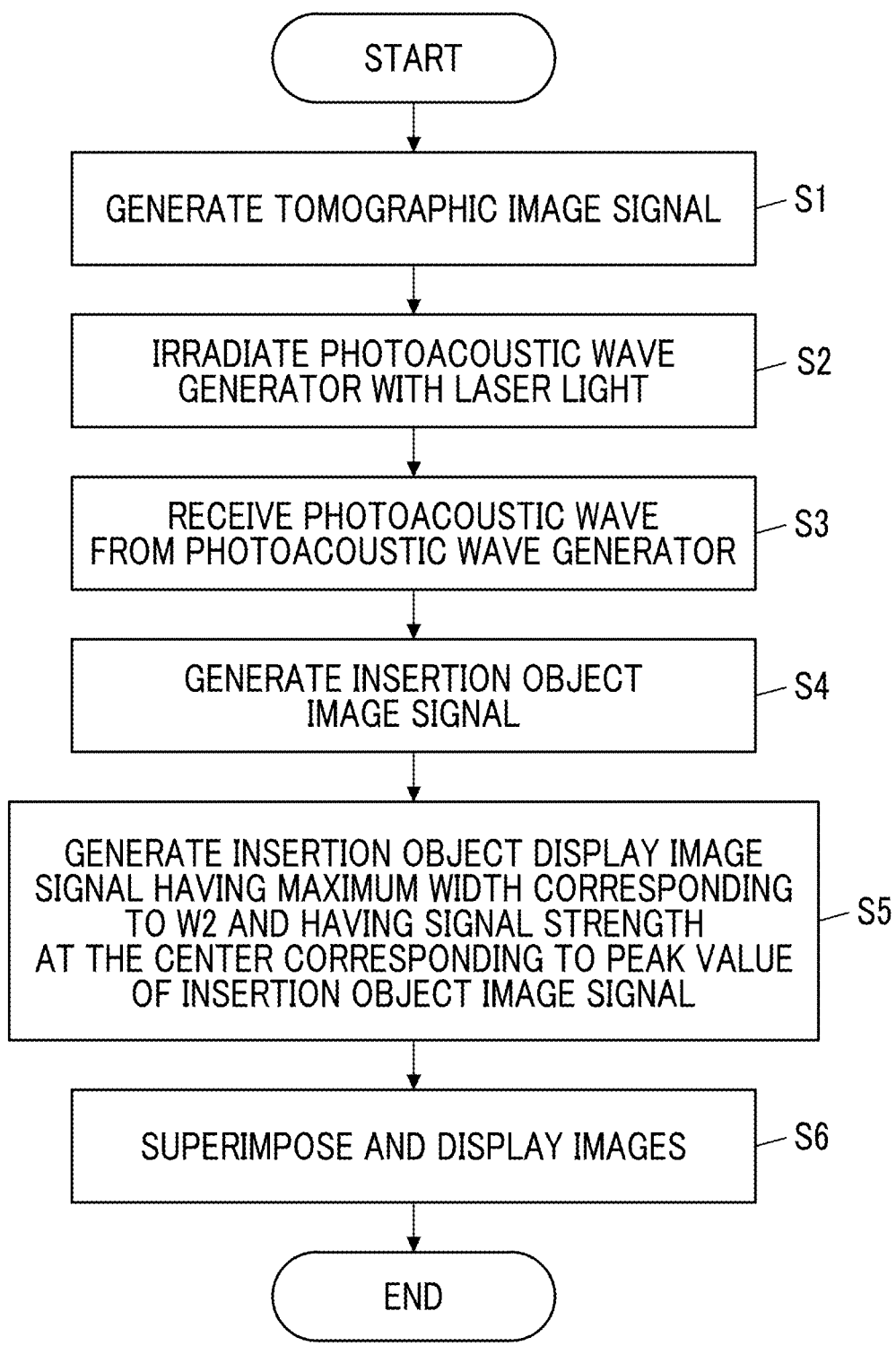
FIG. 7 is a flowchart showing an operation of the ultrasonic wave device according to the first embodiment of the present invention.

Next, an operation of the ultrasonic wave device 1 according to the first embodiment will be described in detail with reference to a flowchart shown in FIG. 7.

First, in step S1, a tomographic image signal that represents a tomographic image of a subject is generated. Here, first, an ultrasonic echo is emitted from a tissue of the subject by irradiating the inside of the subject with an ultrasonic beam from the array transducer 2, and then, the ultrasonic echo is received by the array transducer 2, so that a tomographic image generating reception signal is generated. The tomographic image signal generator 6 generates a tomographic image signal on the basis of the tomographic image generating reception signal obtained in this way.

Next, in step S2, laser beam is applied to the photoacoustic wave generator 21 of the insertion object 13 from the insertion object laser light source 14. Thus, a photoacoustic wave is generated from the photoacoustic wave generator 21.

In the following step S3, the array transducer 2 receives the photoacoustic wave from the photoacoustic wave generator 21, and generates an insertion object image generating reception signal.

In step S4, the insertion object image generating reception signal is output to the insertion object image signal generator 10 through the data separator 5, and an insertion object image signal is generated by the insertion object image signal generator 10.

Figure 8:
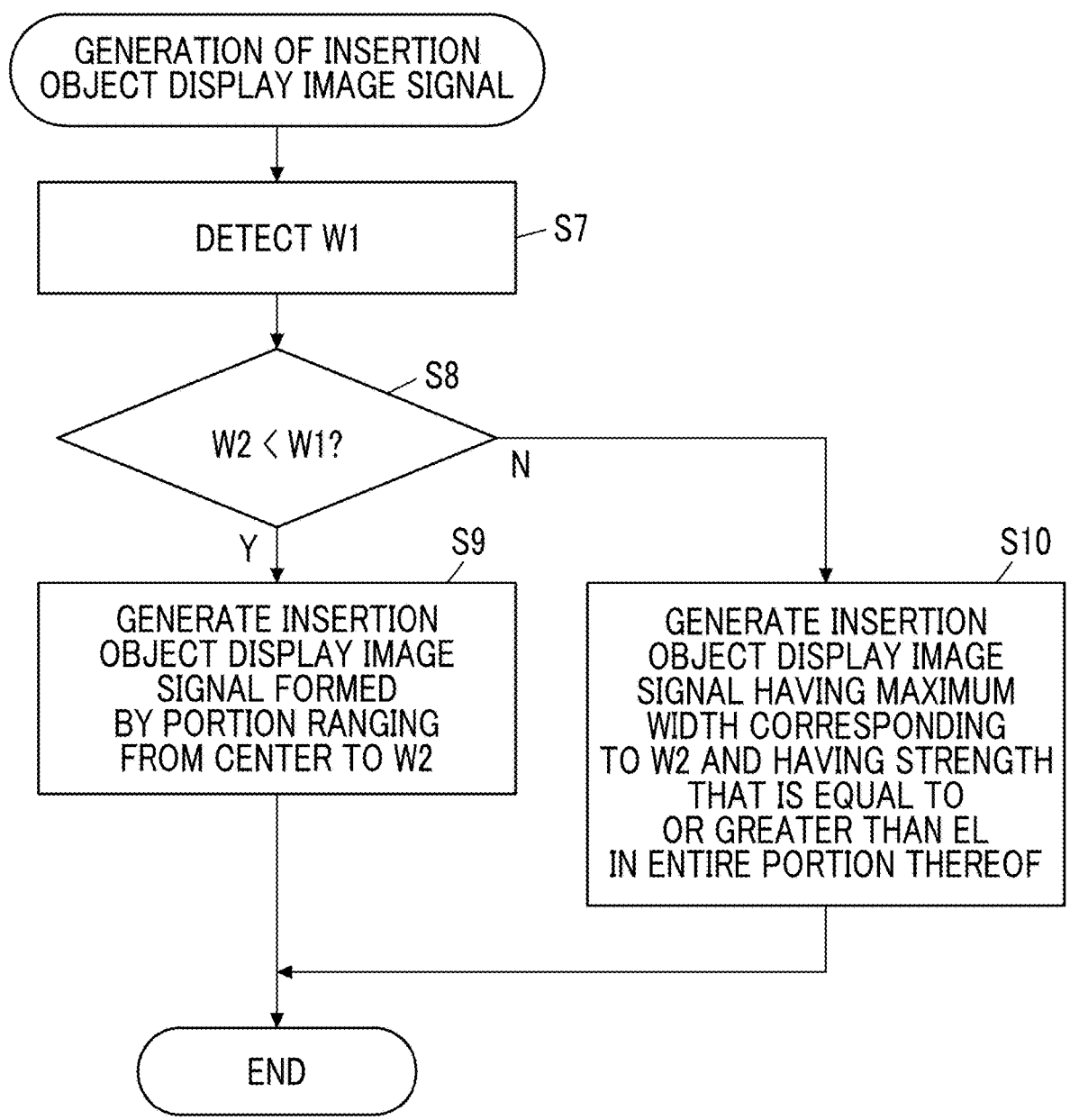
FIG. 8 is a flowchart showing an operation of generating an insertion object display image signal according to the first embodiment of the present invention.

In the following step S5, an insertion object display image signal having a center at a peak position where a signal strength of the insertion object image signal generated in step S4 becomes a peak value, having a maximum width corresponding to a predetermined reference signal width W2, and having a signal strength corresponding to the peak value of the insertion object image signal at the peak position, is generated. More specifically, in step S5, a process shown in the flowchart of FIG. 8 is performed. As shown in FIG. 8, step S5 includes steps S7 to S10.

Figure 9:
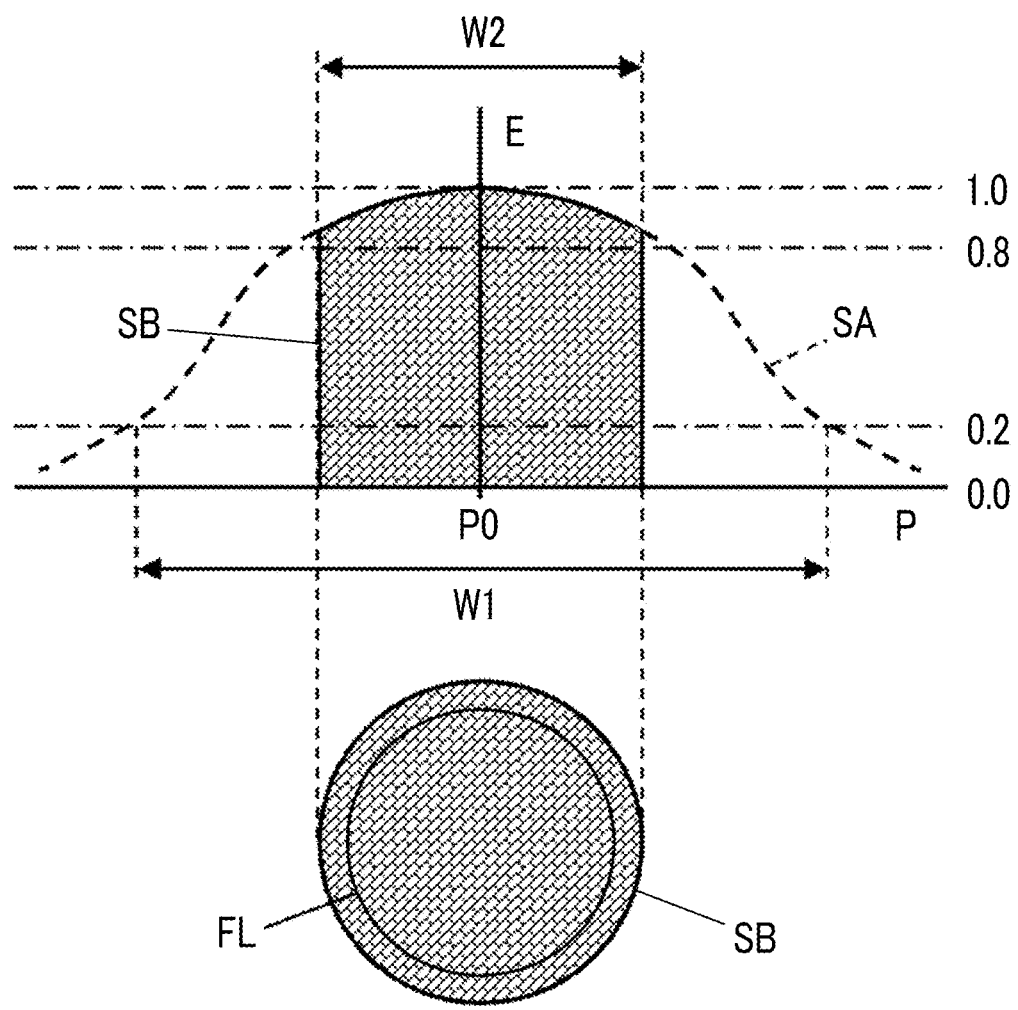
FIG. 9 is a conceptual diagram showing an insertion object display image signal in a case where a first signal width of an insertion object image signal is larger than a reference signal width in the first embodiment of the present invention.

First, in step S7, the first signal width detector 11 detects a first signal width W1 of the insertion object image signal generated in step S4. Here, the first signal width detector 11 detects, as the first signal width, a signal width of an insertion object image signal having a signal strength of a predetermined ratio to a peak value of the insertion object image signal. For example, in a case where the signal strength of the predetermined ratio to the peak value of the insertion object image signal is 20% of the peak value of the insertion object image signal, as shown in FIG. 9, the first signal width detector 11 detects a signal width W1 of an insertion object image signal SA having a signal strength of 0.2, which is 20% of 1.0 that is a peak value of a signal strength E of the insertion object image signal SA, as the first signal width W1. Here, the insertion object image signal SA shown in FIG. 9 is a signal standardized so that the peak value of the signal strength E is 1.0, and in a case where the insertion object image signal SA is shown in the following description, similarly, an image signal standardized so that the peak value is 1.0 is shown.

In step S8, the insertion object display image signal generator 12 determines whether or not the first signal width W1 detected in step S7 is larger than the predetermined reference signal width W2. In a case where the first signal width W1 is larger than the reference signal width W2, the insertion object display image signal generator 12 generates an insertion object display image signal having a center at a peak position where the signal intensity E of the insertion object image signal SA becomes the peak value and formed by a portion ranging from the center to the reference signal width W2, in the insertion object image signals SA, in step S9.

For example, as shown in FIG. 9, the insertion object display image signal generator 12 sets a portion having a center at the peak position P0 where the signal strength E becomes the peak value of 1.0 and ranging from the center to the predetermined reference signal width W2, in the insertion object image signal SA, as an insertion object display image signal SB. Here, a thin line FL in FIG. 9 represents an iso-strength line of the signal strength where the signal strength E is a constant value, for example, 0.9. It can be understood that the insertion object display image signal SB shown in FIG. 9 has small attenuation of the signal strength E and a large signal strength E in a wide range centering around the peak position P0.

In a case where it is determined in step S8 that the first signal width W1 is smaller than the predetermined reference signal width W2, the insertion object display image signal generator 12 proceeds to step S10, and generates an insertion object display image signal SB having a signal strength greater than a predetermined lower limit signal strength EL in an entire portion thereof, from the insertion object image signal SA.

Figure 10:
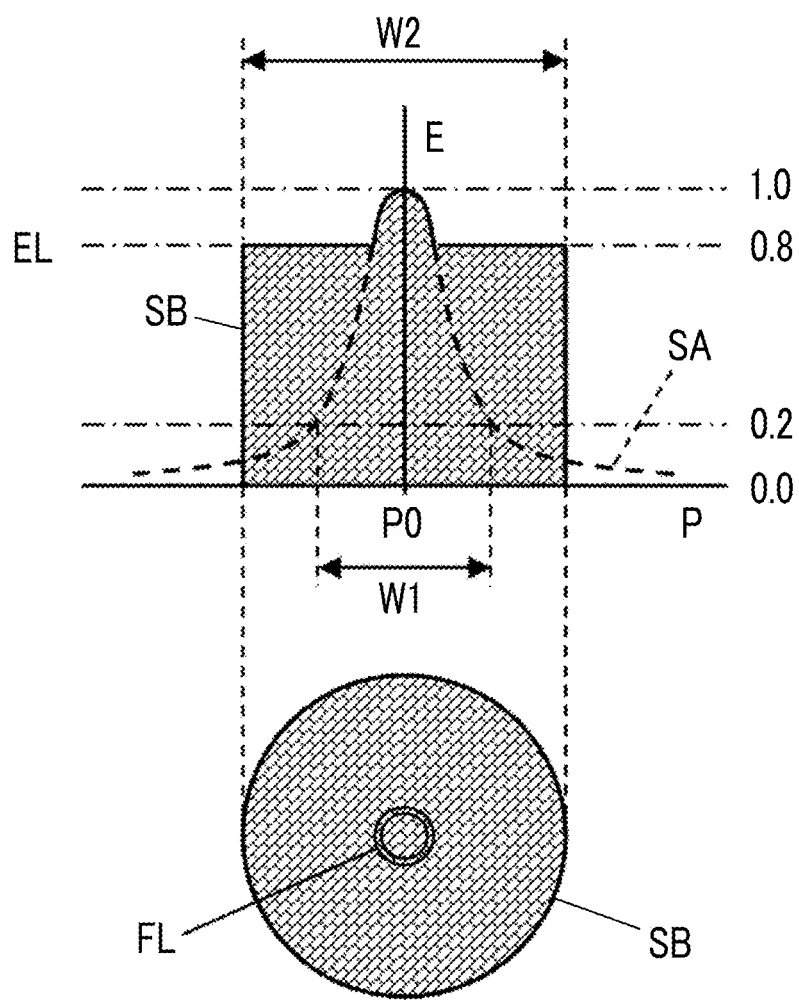
FIG. 10 is a conceptual diagram showing an insertion object display image signal in a case where the first signal width of the insertion object image signal is smaller than the reference signal width in the first embodiment of the present invention.

For example, as shown in FIG. 10, the insertion object display image signal generator 12 sets an image signal obtained by uniformly increasing a signal strength of a portion having a signal strength smaller than a lower limit signal strength EL of 0.8, in the insertion object image signal SA, in a region having a center at a peak position P0 of the insertion object image signal SA and ranging from the peak position P0 to the reference signal width W2 up to 0.8, as the insertion object display image signal SB. Here, two thin lines FL in FIG. 10 indicate iso-strength lines of the signal strengths E of 0.9 and 0.8, respectively. As can be understood from these iso-strength lines, the insertion object display image signal SB shown in FIG. 10 has a signal strength greater than 0.8 in a narrow range centering around the peak position P0, and has a uniform signal strength of 0.8 in other portions. As described above, by setting the signal strength E in the entire portion of the insertion object display image signal SB to be larger than the lower limit signal strength EL, it is possible to clearly display the image of the distal end portion FE of the insertion object 13 on the display 9.

As described above, the process of step S5 is completed as the insertion object display image signal SB is generated in step S9 or step S10.

In a case where the insertion object display image signal SB is generated in step S5, in step S6, the image superposing unit 7 superimposes the tomographic image of the subject and the image of the distal end portion FE of the distal end portion FE of the insertion object 13 on the basis of the insertion object display image signal SB and the tomographic image signal generated in step S1 to be displayed on the display 9. In a case where the tomographic image of the subject and the image of the distal end portion FE of the insertion object 13 are superimposed and displayed on the display 9, the operation of the ultrasonic wave device 1 according to the first embodiment ends.

Figure 11:
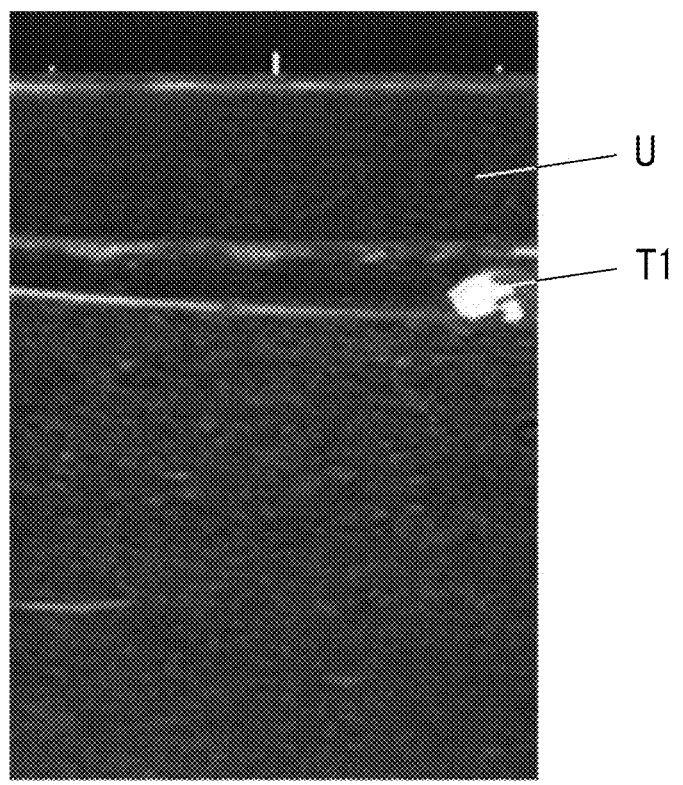
FIG. 11 is a diagram showing an example of the image of the distal end portion of the insertion object displayed in the related-art acoustic wave device.

Here, in a related-art acoustic wave device such as a ultrasonic wave device that includes an insertion object having a photoacoustic wave generator at a distal end portion thereof and generates a tomographic image of a subject, for example, in a case where a distal end portion of the insertion object is inserted into a blood vessel, as a maximum signal strength of an insertion object image generating reception signal corresponding to a photoacoustic wave from the photoacoustic wave generator becomes large, the photoacoustic wave in the vicinity of the distal end portion of the insertion object is not easily attenuated, and thus, a display width of an image of the distal end portion of the insertion object tends to become large. Accordingly, in the related-art acoustic wave device, for example, as shown in FIG. 11, an image T1 of the distal end portion of the insertion object in which an artifact has occurred is superimposed on a tomographic image U of the subject to be displayed on the display. This makes it difficult for a user to visually recognize a tissue or the like of the subject included in the tomographic image U, and thus, it is difficult for the user to confirm an accurate position of the distal end portion of the insertion object.

Figure 12:
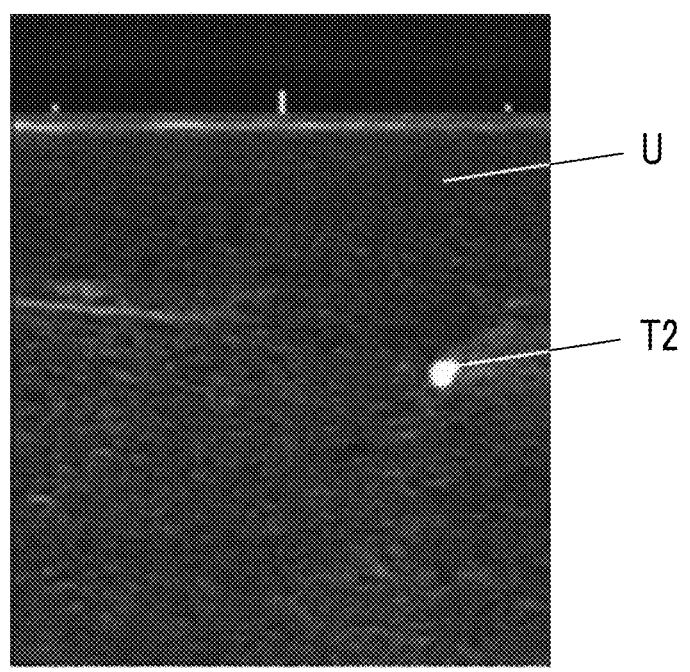
FIG. 12 is a diagram showing an example of the image of the distal end portion of the insertion object displayed in the ultrasonic wave device according to the first embodiment of the present invention.

On the other hand, according to the ultrasonic wave device 1 according to the first embodiment of the present invention, the insertion object display image signal SB having the display width corresponding to the predetermined reference signal width W2 is generated. Accordingly, even in a case where a maximum signal strength of an insertion object image generating reception signal corresponding to a photoacoustic wave from the photoacoustic wave generator 21 becomes large, it is possible to constantly set a maximum width of an image of the distal end portion FE of the insertion object 13 to a width corresponding to the uniform reference signal width W2. Accordingly, according to the ultrasonic wave device 1, for example, as shown in FIG. 12, an image T2 of the distal end portion FE of the insertion object 13 in which the influence of an artifact is suppressed may be superimposed on the tomographic image U of the subject to be displayed on the display 9. Accordingly, it is possible to prevent a situation where the tissue of the subject included in the tomographic image U is not easily visually recognized by a user, to thereby make it possible for the user to accurately confirm the position of the distal end portion FE of the insertion object 13.

In addition, in the related-art acoustic wave device provided with the insertion object having the photoacoustic wave generator at the distal end portion thereof, for example, the size of an image of the distal end portion of the insertion object displayed on the display may change due to a position and an inclination of the insertion object, a contact state of a probe and a subject, a state of the acoustic wave device, aging of the insertion object, a state of the photoacoustic wave generator, and the like. In a case where the size of the image of the distal end portion of the insertion object changes in this way, a user who is visually recognizing the image of the distal end portion of the insertion object may have a sense of discomfort, which may result in a trouble in a procedure for operating the insertion object.

However, according to the ultrasonic wave device 1 according to the first embodiment of the present invention, since the maximum width of the image of the distal end portion FE of the insertion object 13 is constantly set to the display width corresponding to the reference signal width W2, it is possible to suppress a sense of discomfort of a user in recognizing the image of the distal end portion FE of the insertion object 13, and to prevent the trouble in the procedure for operating the insertion object 13.

Further, as shown in FIGS. 9 and 10, the insertion object display image signal SB generated in the first embodiment has a signal waveform in which the signal strength E attenuates as it moves away from the peak position P0 in at least a region near the peak position P0 having a center at the peak position P0, and particularly, has the lower limit signal strength EL that is uniformly determined in a region outside a predetermined region having a center at the peak position P0 in a case where the first signal width W1 of the insertion object image signal SA is smaller than the reference signal width W2. Accordingly, according to the ultrasonic wave device 1 of the first embodiment, it is possible for a user to clearly visually recognize an image of the distal end portion FE of the insertion object 13 corresponding to the insertion object display image signal SB, and to easily confirm the peak position P0.

In the first embodiment, the insertion object image signal SA is generated in steps S2 to S4 after the tomographic image signal is generated in step S1, but the tomographic image signal may be generated after the insertion object image signal SA is generated.

In step S10 in the operation of generating the insertion object display image signal SB, the insertion object display image signal SB as shown in FIG. 10 is generated, but the insertion object display image signal SB having a signal waveform different from the signal waveform of the insertion object display image signal SB shown in FIG. 10 may be generated as long as an image of the distal end portion FE of the insertion object 13 can be clearly displayed on the display 9.

Figure 13:
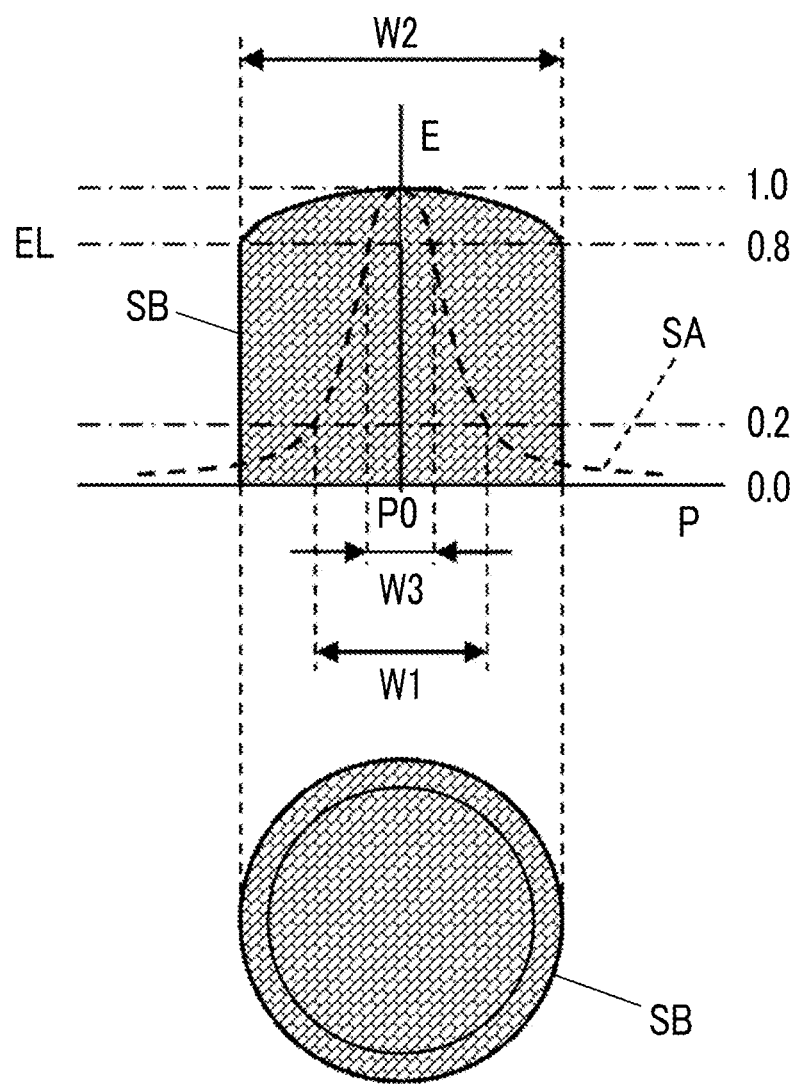
FIG. 13 is a conceptual diagram showing an insertion object display image signal in a case where a first signal width of an insertion object image signal is smaller than a reference signal width in a modification example of the first embodiment of the present invention.

For example, in step S10, the insertion object display image signal generator 12 may generate an insertion object display image signal SB obtained by enlarging a signal width having a portion having a signal strength larger than the lower limit signal strength EL, in the insertion object image signal SA, up to the reference signal width W2. More specifically, as shown in FIG. 13, for example, the insertion object display image signal generator 12 sets the lower limit signal strength EL to 0.8, and sets an image signal obtained by enlarging a signal width W3 of a portion having a signal strength larger than 0.8, in the insertion object image signal SA, up to the reference signal width W2, as the insertion object display image signal SB. As the insertion object display image signal SB having such a signal waveform is generated, it is possible for a user to clearly visually recognize an image of the distal end portion FE of the insertion object 13 corresponding to the insertion object display image signal SB, and to easily confirm the peak position P0.

In a case where the first signal width W1 of the insertion object image signal SA is equal to the reference signal width W2 in step S8, the procedure may proceed to step S9, and the insertion object display image signal generator 12 may generate an insertion object display image signal formed by a portion having a center at a peak position where the signal strength E of the insertion object image signal SA becomes a peak value and ranging from the center to the reference signal width W2, in the insertion object image signal SA. Alternatively, the procedure proceeds to step S10, and the insertion object display image signal generator 12 may generate an insertion object display image signal SB having a signal strength larger than the predetermined lower limit signal strength EL in an entire portion thereof, from the insertion object image signal SA.

Second Embodiment

According to the first embodiment, since the insertion object display image signal SB adjusted so that a maximum width is equal to the reference signal width W2 is generated, as a result, there is a case where the insertion object display image signal SB becomes an image signal of which the maximum width is enlarged or reduced with respect to the first signal width W1 of the insertion object image signal SA. Accordingly, it is possible to cause a user to recognize whether the maximum width of the insertion object display image signal SB corresponding to the image of the distal end portion FE of the insertion object 13 is enlarged or reduced from the first signal width W1 of the insertion object image signal SA, and thus, it is possible to urge the user to pay attention to a positional relationship of the distal end portion FE of the insertion object 13 in the subject.

Figure 14:
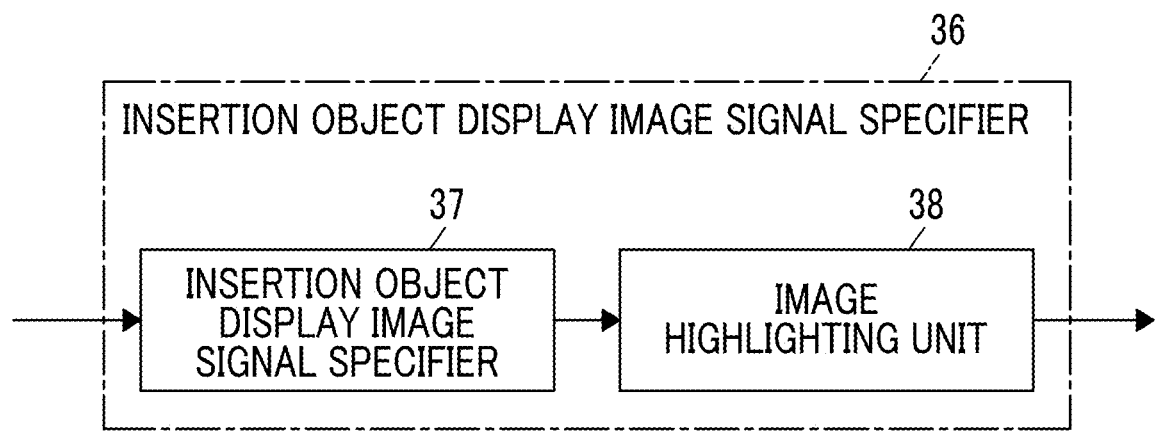
FIG. 14 is a block diagram showing an internal configuration of an insertion object display image signal generator according to a second embodiment of the present invention.

An ultrasonic wave device that is an acoustic wave device according to a second embodiment is different from the ultrasonic wave device 1 according to the first embodiment shown in FIG. 1 in that an insertion object display image signal generator 36 shown in FIG. 14 is used instead of the insertion object display image signal generator 12. Except this difference, the ultrasonic wave device according to the second embodiment has the same configurations as in the ultrasonic wave device 1 according to the first embodiment. The insertion object display image signal generator 36 according to the second embodiment has a configuration in which an insertion object display image signal specifier 37 and an image highlighting unit 38 are connected in series.

The insertion object display image signal specifier 37 of the insertion object display image signal generator 36 specifies an insertion object display image signal SB generated on the basis of an insertion object image signal SA. The insertion object display image signal specifier 37 performs the same process as that performed by the insertion object display image signal generator 12 in the first embodiment for the insertion object image signal SA.

In a case where a maximum width of the insertion object display image signal SB is different from the first signal width W1 of the insertion object image signal SA, that is, in a case where the insertion object display image signal SB is an image signal of which the maximum width is enlarged or reduced from the first signal width W1 of the insertion object image signal SA, the image highlighting unit 38 of the insertion object display image signal generator 36 highlights and displays an image of the distal end portion FE of the insertion object 13 on the display 9.

Figure 15:
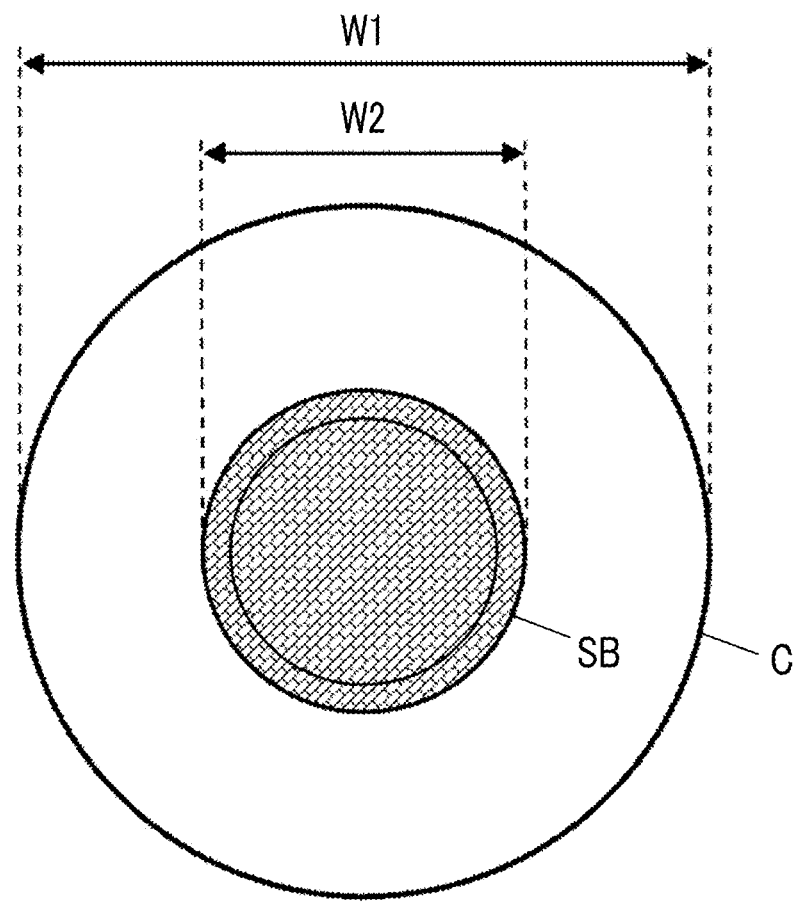
FIG. 15 is a diagram schematically showing an outline of a region having a first signal width larger than a reference signal width according to the second embodiment of the present invention.

For example, the image highlighting unit 38 may superimpose an outline of a region having a center at the peak position P0 of the insertion object image signal SA and having the first signal width W1 on the image of the distal end portion FE of the insertion object 13 of the insertion object image signal SA to be displayed on the display 9. For example, in a case where the first signal width W1 of the insertion object image signal SA is larger than the predetermined reference signal width W2, as shown in FIG. 15, the image highlighting unit 38 generates an outline image signal C having a center at the peak position P0 and corresponding to an outline of a region of the first signal width W1 surrounding the insertion object display image signal SB, and adds the outline image signal C to the insertion object display image signal SB. By recognizing an image of an outline positioned to surround the image of the distal end portion FE of the insertion object 13, it is possible for a user to confirm that the insertion object display image signal SB is an image signal of which the maximum width is reduced from the first signal width W1 of the insertion object image signal SA.

Figure 16:
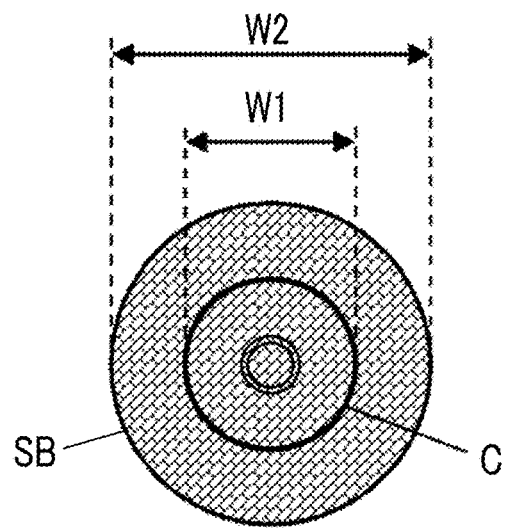
FIG. 16 is a diagram schematically showing an outline of a region having the first signal width smaller than the reference signal width according to the second embodiment of the present invention.

Further, for example, in a case where the first signal width W1 of the insertion object image signal SA is smaller than the predetermined reference signal width W2, as shown in FIG. 16, the image highlighting unit 38 generates an outline image signal C having a center at the peak position P0 and corresponding to the outline of the region of the first signal width W1 included in the insertion object display image signal SB, and adds the outline image signal C to the insertion object display image signal SB. By recognizing an image of an outline positioned to surround the image of the distal end portion FE of the insertion object 13, it is possible for a user to confirm that the insertion object display image signal SB is an image signal of which the maximum width is enlarged from the first signal width W1 of the insertion object image signal SA.

As described above, according to the ultrasonic wave device according to the second embodiment, depending on whether the maximum width of the insertion object display image signal SB is enlarged or reduced from the first signal width W1 of the insertion object image signal SA, the image of the distal end portion FE of the insertion object 13 is highlighted and displayed. Accordingly, it is possible to make a user recognize whether the maximum width of the image of the distal end portion FE of the insertion object 13 is enlarged or reduced from the first signal width W1 of the insertion object image signal SA, and to urge the user to pay attention to a positional relationship of the distal end portion FE of the insertion object 13 in the subject.

By adding the outline image signal C that represents the outline to the insertion object display image signal SB, the image highlighting unit 38 of the insertion object display image signal generator 36 highlights and displays the image of the distal end portion FE of the insertion object 13, but between a case where the maximum width of the insertion object display image signal SB is reduced from the first signal width W1 and a case where the maximum width is enlarged therefrom, the outlines corresponding to the outline image signals C may be displayed on the display 9 in different display modes. For example, between a case where the maximum width of the insertion object display image signal SB is reduced from the first signal width W1 and a case where the maximum width is enlarged therefrom, the image highlighting unit 38 may display the outlines corresponding to the outline image signals C in different colors. In addition, for example, between a case where the maximum width of the insertion object display image signal SB is reduced from the first signal width W1 and a case where the maximum width is enlarged therefrom, the image highlighting unit 38 may configure the outlines corresponding to the outline image signals C by different types of lines such as a solid line and a broken line. Thus, it is possible for a user to clearly recognize whether the maximum width of the image of the distal end portion FE of the insertion object 13 is enlarged or reduced from the first signal width W1 of the insertion object image signal SA.

In addition, as long as a user can recognize whether the maximum width of the insertion object display image signal SB is enlarged or reduced from the first signal width W1 of the insertion object image signal SA, the highlighting display of the image of the distal end portion FE of the insertion object 13 is not limited to the addition of the outline image signal C to the insertion object display image signal SB.

Figure 17:
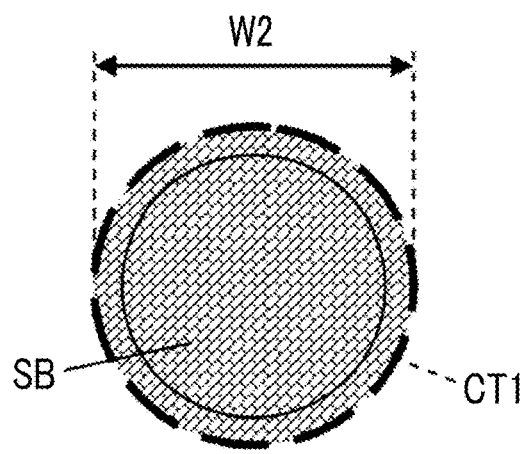
FIG. 17 is a diagram schematically showing an outer peripheral portion of an image of a distal end portion of an insertion object in a case where a first signal width is larger than a reference signal width in a modification example of the second embodiment of the present invention.
Figure 18:
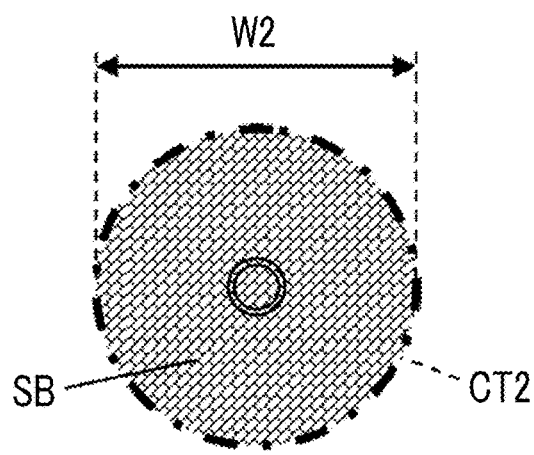
FIG. 18 is a diagram schematically showing an outer peripheral portion of an image of the distal end portion of the insertion object in a case where the first signal width is smaller than the reference signal width in the modification example of the second embodiment of the present invention.

For example, as shown in FIGS. 17 and 18, between a case where the maximum width of the insertion object display image signal SB is reduced from the first signal width W1 of the insertion object image signal SA and a case where the maximum width is enlarged therefrom, the image highlighting unit 38 may set outer peripheral portions CT1 and CT2 of the insertion object display image signal SB in different colors. Here, FIG. 17 shows a case where the maximum width of the insertion object display image signal SB is reduced from the first signal width W1 of the insertion object image signal SA to the reference signal width W2, and FIG. 18 shows a case where the maximum width of the insertion object display image signal SB is enlarged from the first signal width W1 of the insertion object image signal SA to the reference signal width W2. In addition, between a case where the maximum width of the insertion object display image signal SB is reduced from the first signal width W1 of the insertion object image signal SA and a case where the maximum width is enlarged therefrom, the outer peripheral portions CT1 and CT2 of the insertion object display image signal SB may be configured by different types of lines such as a solid line and a broken line, instead of setting the colors of the outer peripheral portions CT1 and CT2 of the insertion object display image signal SB to be different from each other.

Figure 19:
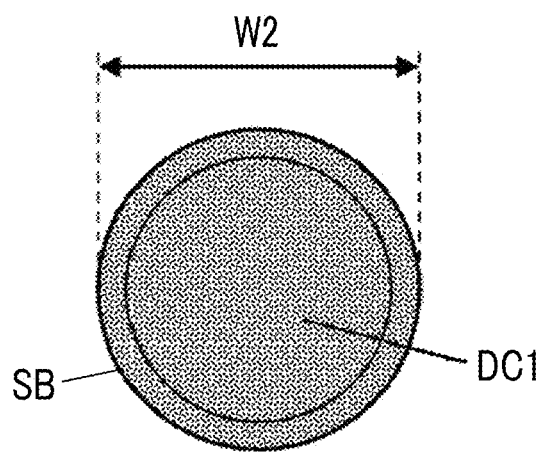
FIG. 19 is a diagram schematically showing an image of a distal end portion of an insertion object in a case where a first signal width is larger than a reference signal width in another modification example of the second embodiment of the present invention.
Figure 20:
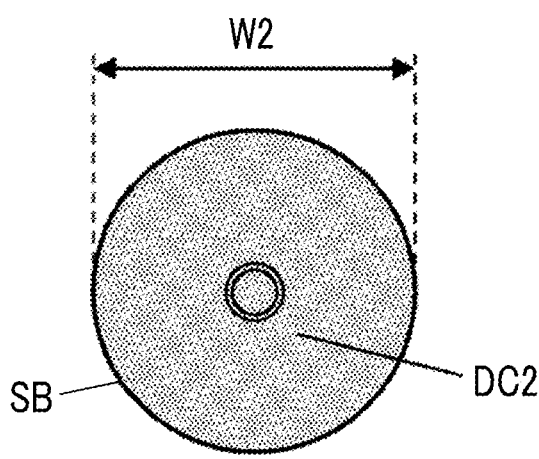
FIG. 20 is a diagram schematically showing an image of the distal end portion of the insertion object in a case where the first signal width is smaller than the reference signal width in the other modification example of the second embodiment of the present invention.

Further, for example, as shown in FIG. 19 and FIG. 20, between a case where the maximum width of the insertion object display image signal SB is reduced from the first signal width W1 of the insertion object image signal SA and a case where the maximum width is enlarged therefrom, the image highlighting unit 38 may set the insertion object display image signal SB in different colors. Here, FIG. 19 shows a case where the maximum width of the insertion object display image signal SB is reduced from the first signal width W1 of the insertion object image signal SA to the reference signal width W2, and shows that the insertion object display image signal SB has a first display color DC1. Further, FIG. 20 shows a case where the maximum width of the insertion object display image signal SB is enlarged from the first signal width W1 of the insertion object image signal SA to the reference signal width W2, and shows that the insertion object display image signal SB has a second display color DC2.

Third Embodiment

The insertion object display image signal generator 12 in the first embodiment generates an insertion object display image signal SB having a signal waveform in which the signal strength E attenuates as it moves away from the peak position P0 in at least a region near the peak position P0 having a center at the peak position P0, but a configuration in which the insertion object display image signal SB has such a signal waveform is not limiting as long as a user can clearly visually recognize an image of the distal end portion FE of the insertion object 13.

Although not shown, an ultrasonic wave device that is an acoustic wave device according to a third embodiment has the same configuration as in the ultrasonic wave device 1 according to the first embodiment shown in FIG. 1.

An insertion object display image signal generator according to the third embodiment may generate an insertion object display image signal SB having a center at the peak position P0 of the insertion object image signal SA, having a maximum width corresponding to the reference signal width W2, and having a signal strength corresponding to a peak value of the insertion object image signal SA in an entire portion thereof.

Figure 21:
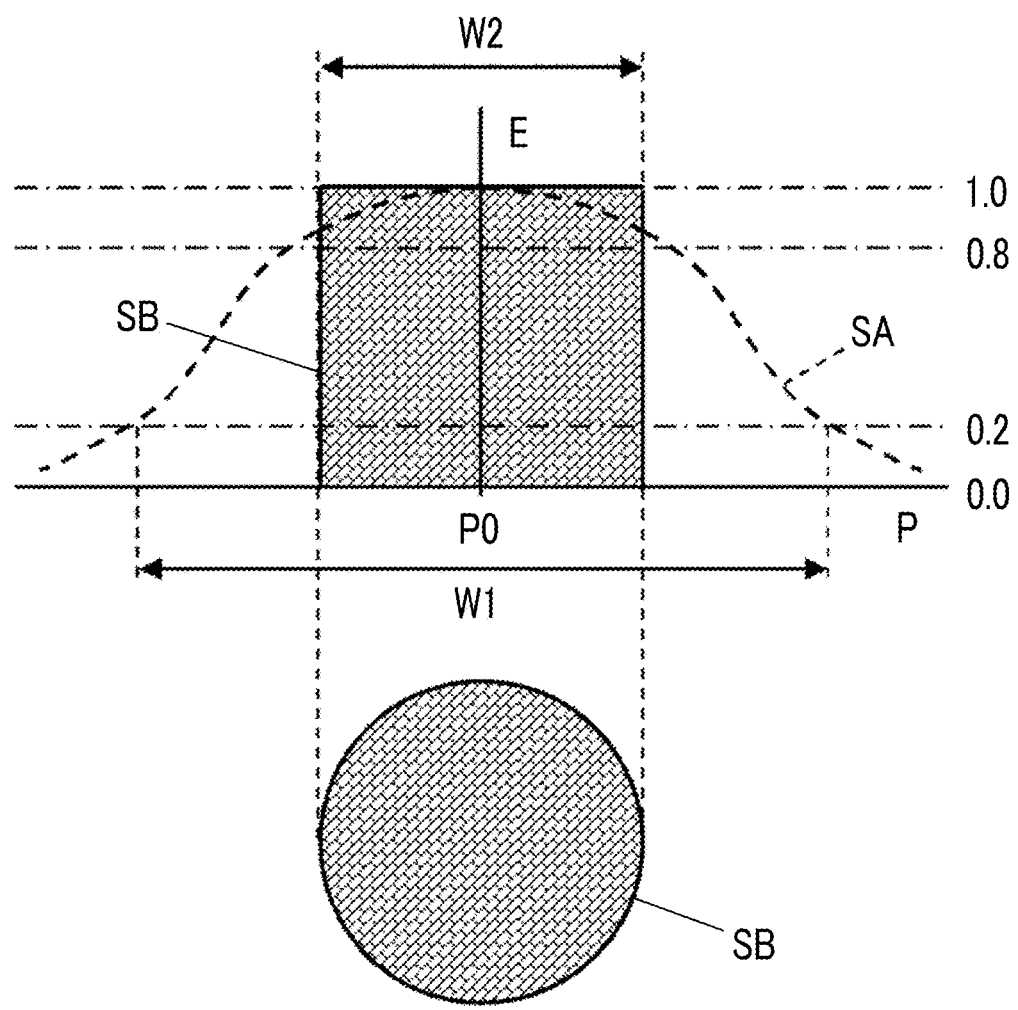
FIG. 21 is a diagram schematically showing an insertion object display image signal in a case where a first signal width is larger than a reference signal width in a third embodiment of the present invention.
Figure 22:
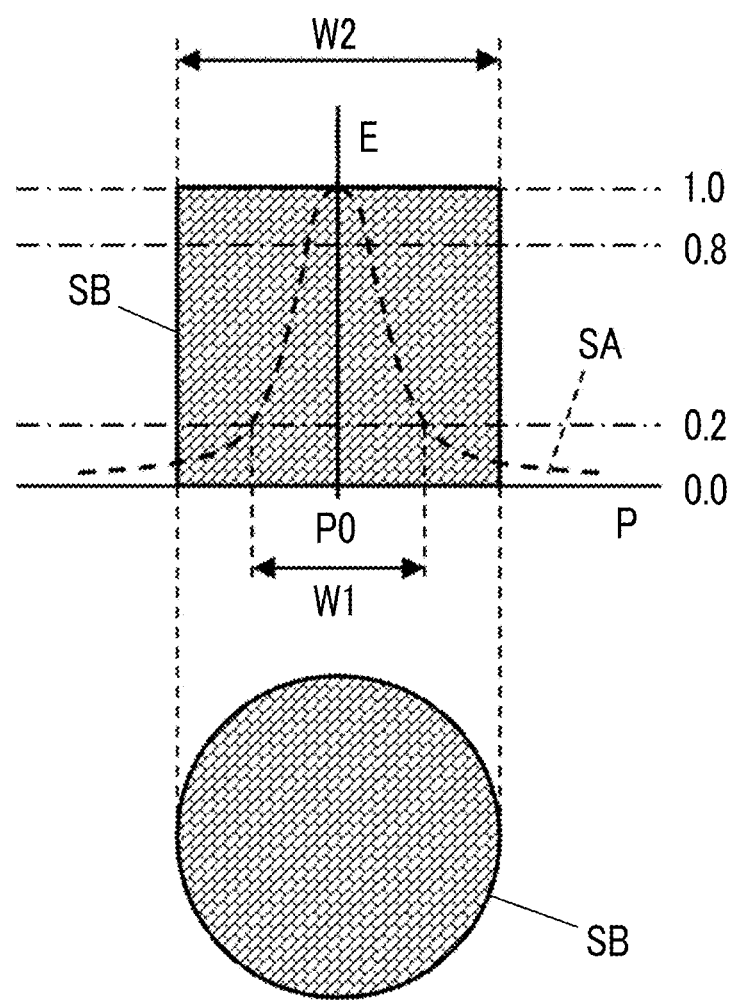
FIG. 22 is a diagram schematically showing an insertion object display image signal in a case where the first signal width is smaller than the reference signal width in the third embodiment of the present invention.

For example, as shown in FIGS. 21 and 22, the insertion object display image signal generator sets an image signal in which all the signal strengths E are uniformly set to the peak value of 1.0 of the insertion object image signal SA in a region having a center at the peak position P0 of the insertion object image signal SA and ranging from the peak position P0 to the predetermined reference signal width W2, in the insertion object image signal SA, as the insertion object display image signal SB. Here, FIG. 21 shows the insertion object display image signal SB in a case where the first signal width W1 of the insertion object image signal SA is larger than the reference signal width W2, and FIG. 22 shows the insertion object display image signal SB in a case where the first signal width W1 is smaller than the reference signal width W2.

As described above, according to the ultrasonic wave device of the third embodiment, since an entire portion has a signal strength corresponding to the peak value of the signal strength E of the insertion object image signal SA in a region having a center at the peak position P0 of the insertion object image signal SA and having a width corresponding to the reference signal width W2, it is possible to clearly display an image of the distal end portion FE of the insertion object 13 corresponding to the insertion object display image signal SB on the display 9. Accordingly, the user is able to clearly visually recognize the image of the distal end portion FE of the insertion object 13.

Fourth Embodiment

By adding a center marker having a center at a position corresponding to the peak position P0 of the insertion object image signal SA to an image of the distal end portion FE of the insertion object 13 corresponding to the insertion object display image signal SB generated in the third embodiment, it is possible for a user to clearly confirm the center position of the image of the distal end portion FE of the insertion object 13.

Although not shown, an ultrasonic wave device that is an acoustic wave device according to the fourth embodiment has the same configuration as in the ultrasonic wave device 1 according to the first embodiment shown in FIG. 1.

Figure 23:
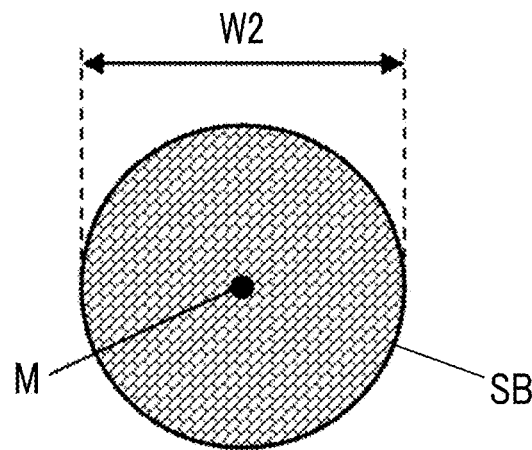
FIG. 23 is a diagram schematically showing an insertion object image signal according to a fourth embodiment of the present invention.

As shown in FIG. 23, an insertion object display image signal generator according to the fourth embodiment may add a center marker image signal M that represents the peak position P0 of the insertion object image signal SA to the insertion object display image signal SB. Thus, it is possible to superimpose a center marker corresponding to the center marker image signal M on an image of the distal end portion FE of the insertion object 13 corresponding to the insertion object display image signal SB to be displayed on the display 9.

As described above, according to the ultrasonic wave device of the fourth embodiment, since the center marker is added to the image of the distal end portion FE of the insertion object 13, it is possible for a user to clearly confirm a center position of the image of the distal end portion FE of the insertion object 13.

Further, for example, the insertion object display image signal generator according to the fourth embodiment may include the image highlighting unit 38 in the second embodiment shown in FIG. 14, and thus, the image of the distal end portion FE of the insertion object 13 may be appropriately highlighted and displayed depending on whether the first signal width W1 of the insertion object image signal SA is reduced or enlarged with reference to the reference signal width W2.

Figure 24:
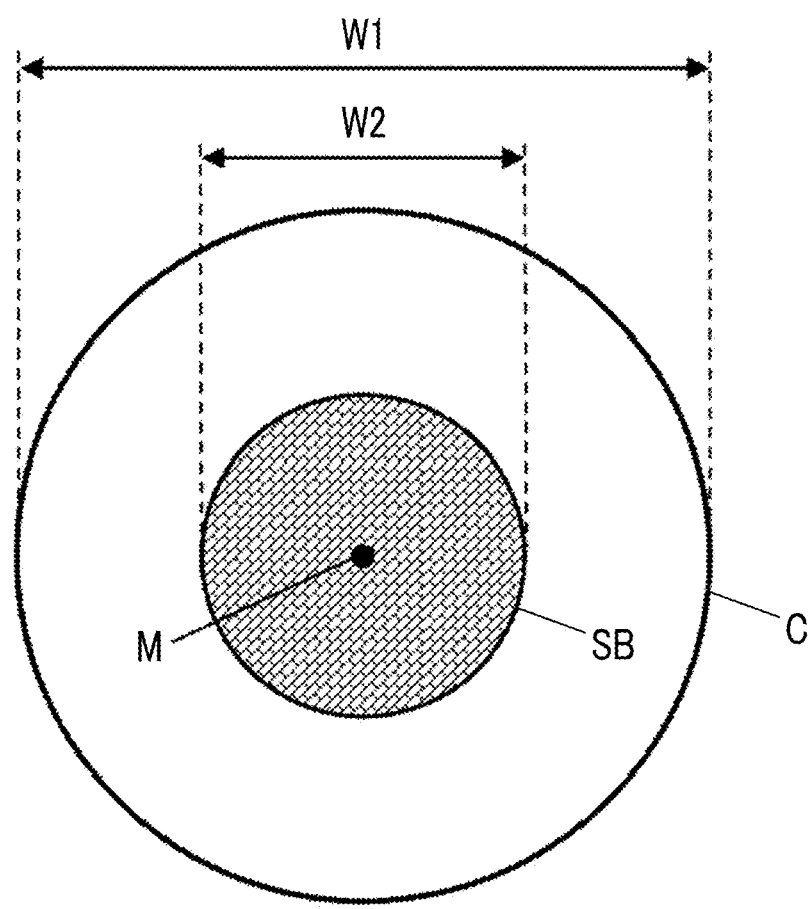
FIG. 24 is a diagram schematically showing an insertion object display image signal in a case where a first signal width is larger than a reference signal width in a modification example of the fourth embodiment of the present invention.
Figure 25:
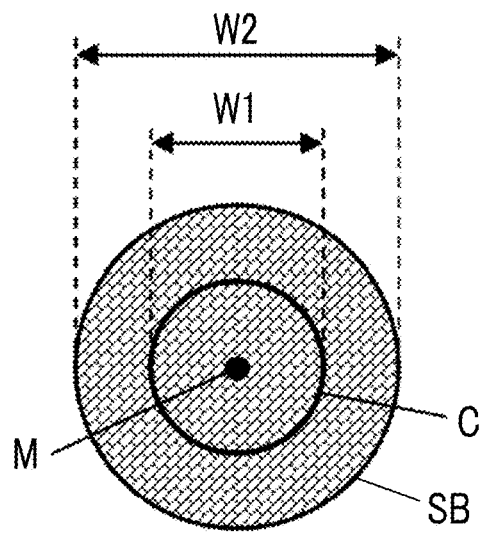
FIG. 25 is a diagram schematically showing an insertion object display image signal in a case where the first signal width is smaller than the reference signal width in the modification example of the fourth embodiment of the present invention.

For example, as shown in FIGS. 24 and 25, the insertion object display image signal generator may further add the outline image signal C to the insertion object display image signal SB to which the center marker image signal M is added. Here, FIG. 24 shows the insertion object display image signal SB in a case where the first signal width W1 of the insertion object image signal SA is larger than the reference signal width W2, and FIG. 25 shows the insertion object display image signal SB in a case where the first signal width W1 of the insertion object image signal SA is smaller than the reference signal width W2.

Figure 26:
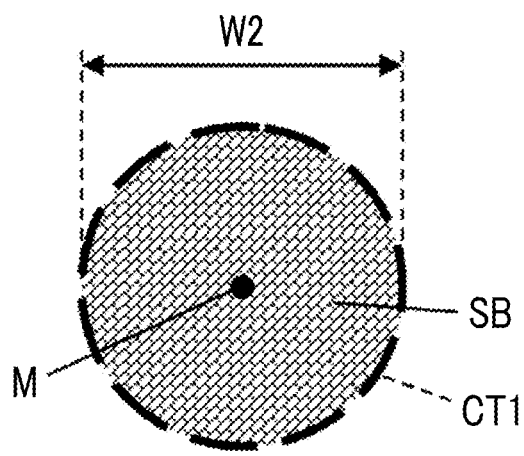
FIG. 26 is a diagram schematically showing an insertion object display image signal in a case where a first signal width is larger than a reference signal width in another modification example of the fourth embodiment of the present invention.
Figure 27:
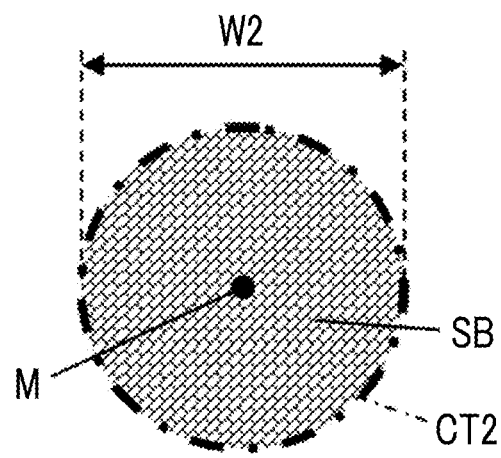
FIG. 27 is a diagram schematically illustrating an insertion object display image signal in a case where the first signal width is smaller than the reference signal width in the other modification example of the fourth embodiment of the present invention.

Further, as shown in FIGS. 26 and 27, for example, the insertion object display image signal generator may set display colors of outer peripheral portions CT1 and CT2 of the insertion object display image signal SB to which the center marker image signal M is added to be different from each other, depending on whether the first signal width W1 of the insertion object image signal SA is reduced or enlarged with reference to the reference signal width W2. Here, FIG. 26 shows the insertion object display image signal SB in a case where the first signal width W1 of the insertion object image signal SA is larger than the reference signal width W2, and FIG. 27 shows the insertion object display image signal SB in a case where the first signal width W1 of the insertion object image signal SA is smaller than the reference signal width W2.

Figure 28:
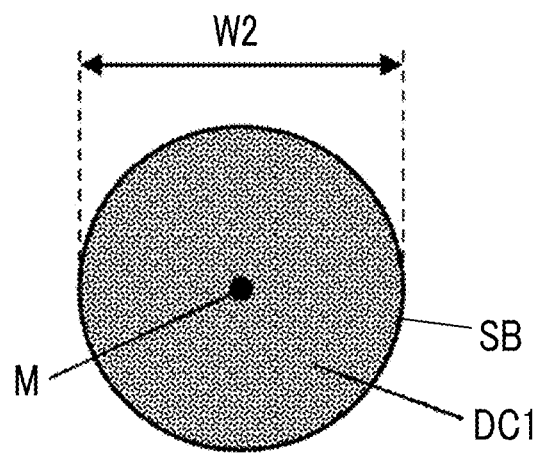
FIG. 28 is a diagram schematically showing an insertion object display image signal in a case where a first signal width is larger than a reference signal width in still another modification example of the fourth embodiment of the present invention.
Figure 29:
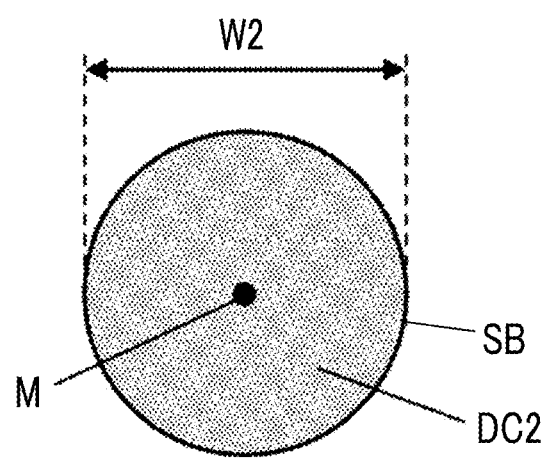
FIG. 29 is a diagram schematically showing an insertion object display image signal in a case where the first signal width is smaller than the reference signal width in the other modification example of the fourth embodiment of the present invention.

Further, for example, the insertion object display image signal generator may add different display colors to the insertion object display image signal SB to which the center marker image signal M is added, depending on whether the first signal width W1 of the insertion object image signal SA is reduced or enlarged with reference to the reference signal width W2, as shown in FIGS. 28 and 29. Here, FIG. 28 shows the insertion object display image signal SB in a case where the first signal width W1 of the insertion object image signal SA is larger than the reference signal width W2, and FIG. 29 shows the insertion object display image signal SB in a case where the first signal width W1 of the insertion object image signal SA is smaller than the reference signal width W2.

Fifth Embodiment

In the first to fourth embodiments, the reference signal width W2 used as the maximum width of insertion object display image signal SB may be set by a user.

Figure 30:
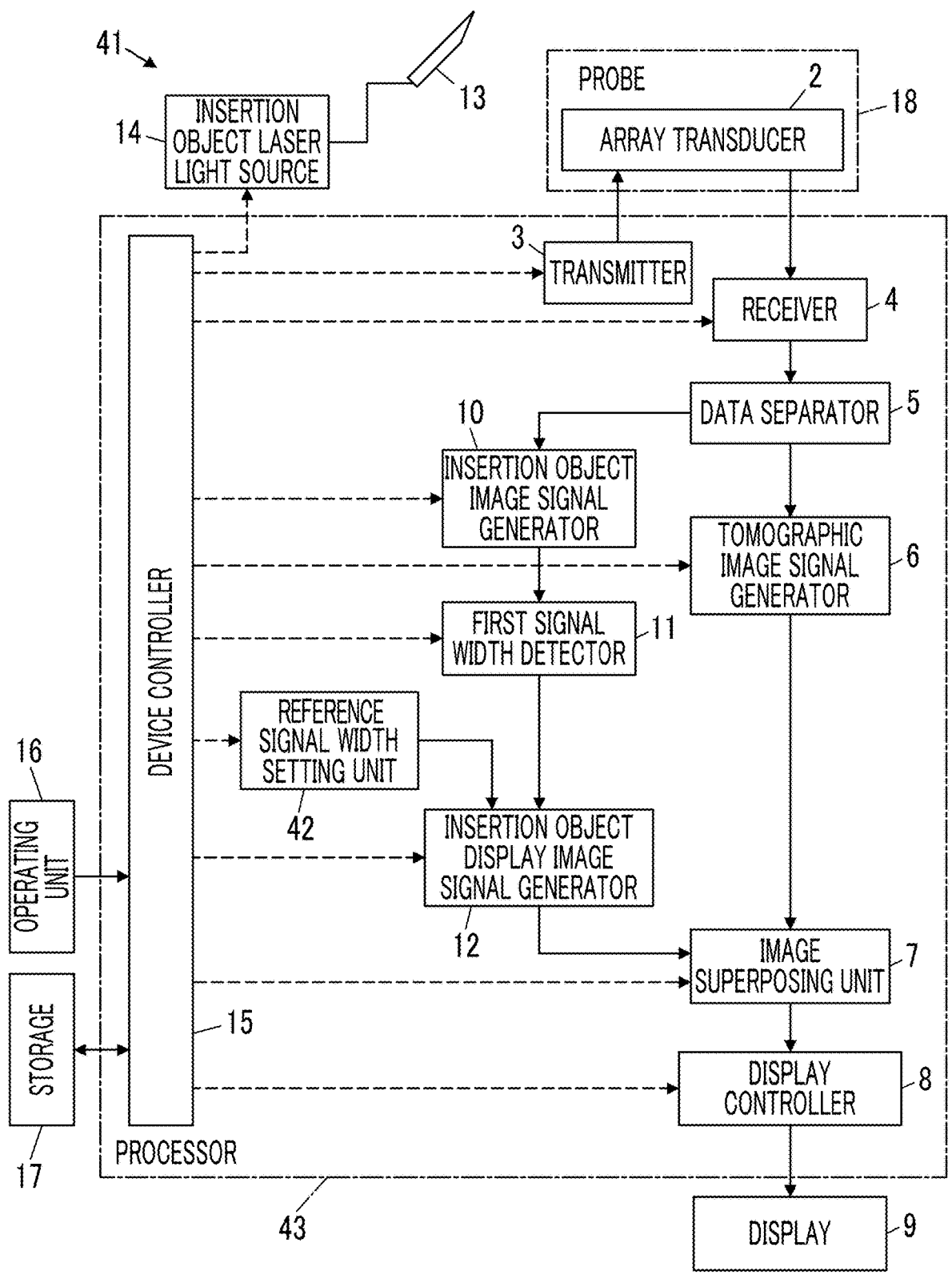
FIG. 30 is a block diagram showing a configuration of an ultrasonic wave device according to a fifth embodiment of the present invention.

FIG. 30 is a block diagram showing a configuration of an ultrasonic wave device 41 that is an acoustic wave device according to a fifth embodiment. The ultrasonic wave device 41 according to the fifth embodiment differs from the ultrasonic wave device 1 according to the first embodiment shown in FIG. 1 in that the ultrasonic wave device 41 further includes a reference signal width setting unit 42 connected to the insertion object display image signal generator 12, in which the device controller 15 is connected to the reference signal width setting unit 42. A processor 43 is configured by the transmitter 3, the receiver 4, the data separator 5, the tomographic image signal generator 6, the image superposing unit 7, the display controller 8, the insertion object image signal generator 10, the first signal width detector 11, the insertion object display image signal generator 12, the device controller 15, and the reference signal width setting unit 42.

The reference signal width setting unit 42 of the processor 43 sets the reference signal width W2 that is the maximum width of the insertion object display image signal SB. For example, the reference signal width setting unit 42 may set a value input by a user through the operating unit 16 as the reference signal width W2.

Thus, according to the ultrasonic wave device 41 according to the fifth embodiment, since a user sets the reference signal width W2 in advance, it is possible to adjust the size of an image of the distal end portion FE of the insertion object 13 so that a tissue or the like included in a tomographic image of a subject can be easily visually recognized while the image of the distal end portion FE of the insertion object 13 can be clearly displayed on the display 9.

Although not shown, for example, as the first signal width detector 11 is connected to the reference signal width setting unit 42, the reference signal width setting unit 42 may set the reference signal width W2 on the basis of the first signal width W1 detected in a calibration medium such as water, ultrasonic jelly, or the like that is different from a subject. For example, more specifically, more specifically, by applying laser beam from the insertion object laser light source 14 to the photoacoustic wave generator 21 of the insertion object 13 while the distal end portion FE of the insertion object 13 is positioned in the calibration medium to generate the insertion object image signal SA, the reference signal width setting unit 42 may set a signal width having a signal strength having a predetermined ratio to the signal strength E of the insertion object image signal SA as the reference signal width W2.

Figure 31:
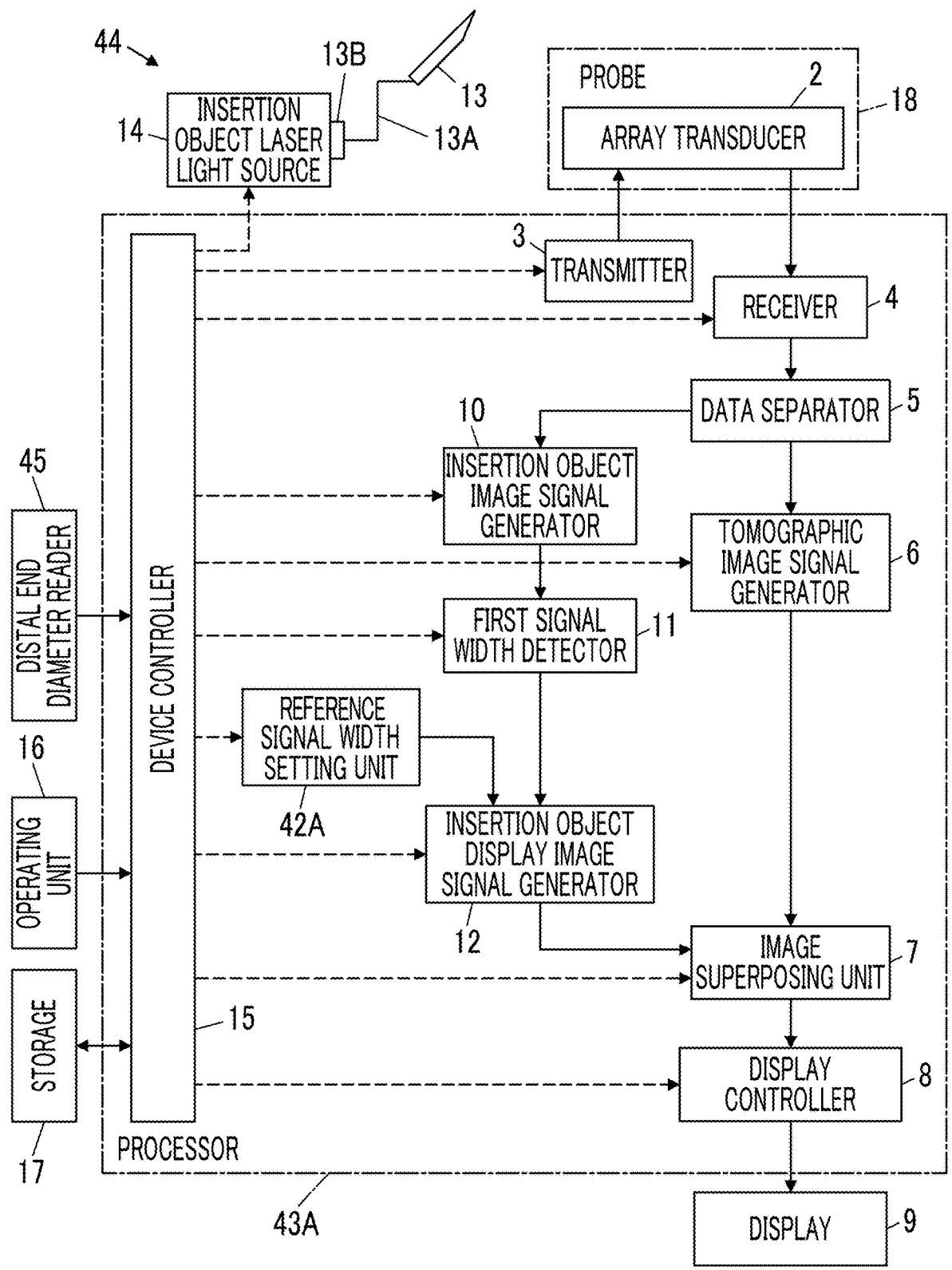
FIG. 31 is a block diagram showing a configuration of an ultrasonic wave device according to a modification example of the fifth embodiment of the present invention.

Further, in the fifth embodiment, the reference signal width setting unit 42 sets a value set by a user as the reference signal width W2, but may set the reference signal width W2 by automatically reading information on the insertion object 13. FIG. 31 is a block diagram showing a configuration of an ultrasonic wave device 44 according to a modification example of the fifth embodiment. The ultrasonic wave device 44 includes a processor 43A having a reference signal width setting unit 42A instead of the processor 43 having the reference signal width setting unit 42, in the ultrasonic wave device 41 according to the fifth embodiment shown in FIG. 30, and further includes a distal end diameter reader 45 connected to the device controller 15.

For example, a distal end diameter recording unit configured by an integrated circuit (IC) tag, a bar code, or the like on which the diameter of the distal end portion FE of the insertion object 13 is recorded is attached at a root portion of the insertion object 13, a cable 13A connected to the insertion object 13, a connector 13B for connecting one end of the cable 13A to the insertion object laser light source 14, and the like, and the distal end diameter reader 45 automatically reads the diameter of the distal end portion FE of the insertion object 13 from the distal end diameter recording unit.

The reference signal width setting unit 42A calculates a converted value by multiplying a value of the diameter read by the distal end diameter reader 45 by a predetermined coefficient, and sets the converted value as the reference signal width W2.

Accordingly, according to the ultrasonic wave device 44 according to the modification example of the fifth embodiment, it is possible to accurately reflect an actual size of the distal end portion FE of the insertion object 13 to the image of the distal end portion FE of the insertion object 13 displayed on the display 9 in a state where a user does not need to input the value of the reference signal width W2.

Sixth Embodiment

The first to fifth embodiments show examples in which the present invention is applied to the ultrasonic wave device that includes the insertion object 13 having the photoacoustic wave generator 21, but the present invention may be applied to a photoacoustic wave device that includes the insertion object 13 having the photoacoustic wave generator 21 and generates a tomographic image of a subject on the basis of photoacoustic waves emitted from a tissue or the like in a subject.

Figure 32:
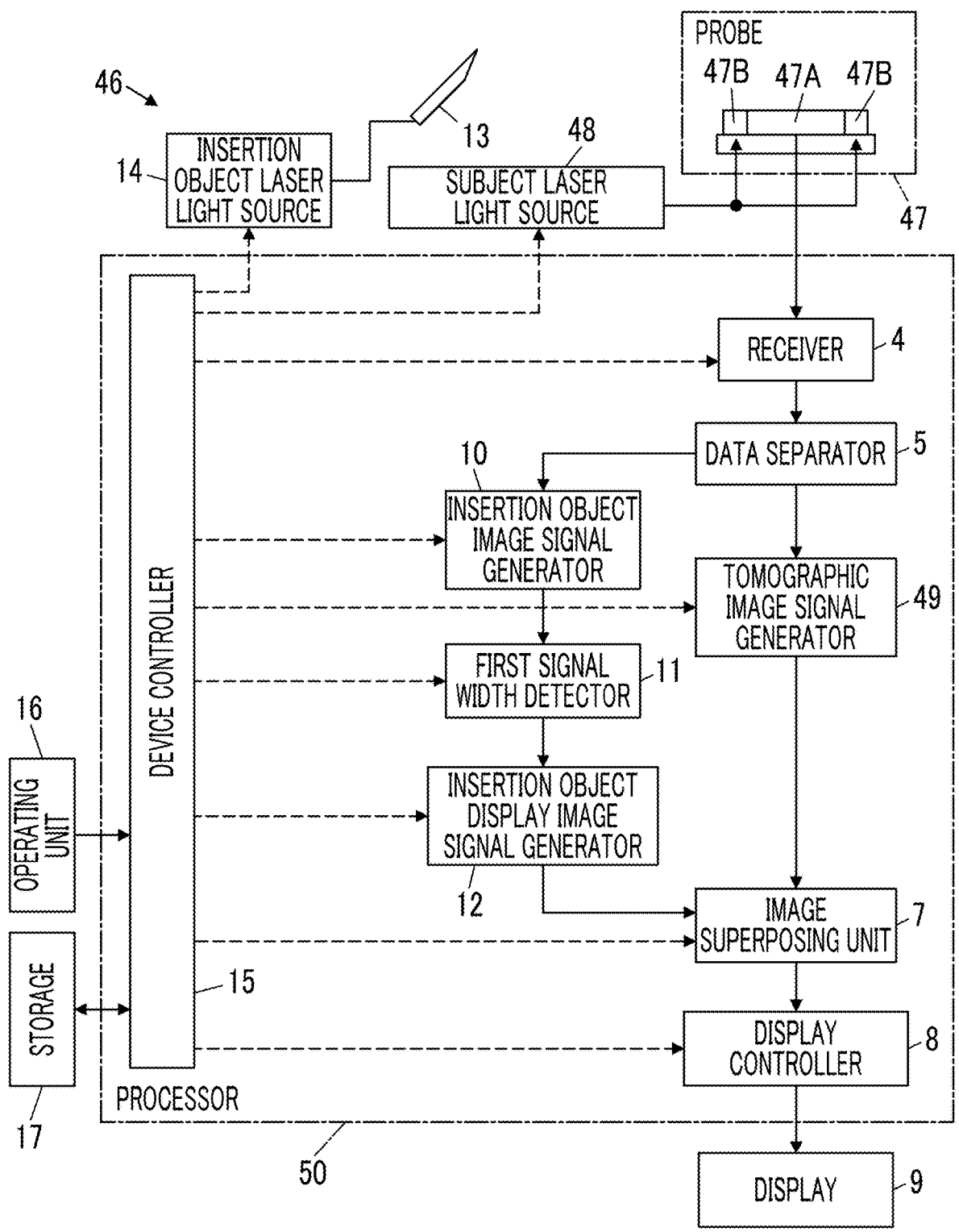
FIG. 32 is a block diagram showing a configuration of a photoacoustic wave device according to a sixth embodiment of the present invention.

FIG. 32 is a block diagram showing a configuration of a photoacoustic wave device 46 that is an acoustic wave device according to the sixth embodiment. In the ultrasonic wave device 1 according to the first embodiment shown in FIG. 1, the photoacoustic wave device 46 includes a probe 47 instead of the probe 18, includes a subject laser light source 48 connected to the probe 47 instead of the transmitter 3, and includes a tomographic image signal generator 49 instead of the tomographic image signal generator 6, and except for these differences, the photoacoustic wave device 46 has the same configurations as in the ultrasonic wave device 1 according to the first embodiment. The probe 47 is configured to include an array transducer 47A and a subject laser beam irradiator 47B disposed adjacent to both ends of the array transducer 47A. The receiver 4 is connected to the array transducer 47A of the probe 47, and the subject laser light source 48 is connected to the two subject laser beam irradiators 47B of the probe 47. The device controller 15 is connected to the subject laser light source 48.

Further, the receiver 4, the data separator 5, the image superposing unit 7, the display controller 8, the insertion object image signal generator 10, the first signal width detector 11, the insertion object display image signal generator 12, the device controller 15, and the tomographic image signal generator 49 form the processor 50.

Although not shown, the subject laser beam irradiator 47B of the probe 47 and the subject laser light source 48 form a subject beam irradiator, and the array transducer 47A of the probe 47 and the receiver 4 form a reception signal generator.

The subject laser light source 48 shown in FIG. 32 has the same internal configuration as in the insertion object laser light source 14, and emits a pulsed laser beam under the control of the device controller 15.

The two subject laser beam irradiators 47B of the probe 47 are connected to the subject laser light source 48 by light guide members (not shown) such as optical fibers, respectively, and irradiate the inside of a subject with a pulsed laser beam from the subject laser light sources 48.

In a case where the pulsed laser beam is applied to a tissue of the subject from the subject laser beam irradiator 47B, in vivo substances such as glucose and hemoglobin included in the tissue of the subject absorb the pulsed laser beam to perform expansion and contraction, and emits an acoustic wave called a so-called photoacoustic wave.

The array transducer 47A of the probe 47 has the same configuration as in the array transducer 2 in the first embodiment shown in FIG. 1, generates a tomographic image generating reception signal on the basis of a photoacoustic wave emitted from the tissue of the subject, and generates an insertion object image generating reception signal on the basis of a photoacoustic wave emitted from the photoacoustic wave generator 21 of the insertion object 13.

The tomographic image generating reception signal generated by the array transducer 47A is output to the tomographic image signal generator 49 through the data separator 5. The tomographic image signal generator 49 has the same configuration as in the tomographic image signal generator 6 in the first embodiment shown in FIG. 1, and generates a tomographic image signal that represents a tomographic image of the subject from the tomographic image generating reception signal generated on the basis of the photoacoustic wave.

On the basis of the tomographic image signal and the insertion object display image signal SB generated by the insertion object display image signal generator 12, the image superposing unit 7 superimposes the tomographic image of the subject and the image of the distal end portion FE of the insertion object 13 to be displayed on the display 9.

As described above, according to the photoacoustic apparatus 46 of the sixth embodiment, similarly to the ultrasonic wave device 1 of the first embodiment shown in FIG. 1, since the insertion object image signal generator 10, the first signal width detector 11, and the insertion object display image signal generator 12 are provided, it is possible to constantly set a maximum width of an image of the distal end portion FE of the insertion object 13 to a width corresponding to the predetermined reference signal width W2. Thus, according to the photoacoustic wave device 46, it is possible to prevent a situation where a tissue of a subject included in a tomographic image of a subject is not easily visually recognized by a user, and it is possible for the user to accurately confirm the position of the distal end portion FE of the insertion object 13. Further, according to the photoacoustic wave device 46, it is possible to suppress a sense of discomfort of a user in visually recognizing the image of the distal end portion FE of the insertion object 13, and to prevent the trouble in the procedure for operating the insertion object 13 by the user.

The various configurations described in the second to fifth embodiments may be also appropriately applied to the photoacoustic wave device 46 of the sixth embodiment.

As described above, according to the first to sixth embodiments of the present invention, the following technical ideas are disclosed.

(Appendix 1) An acoustic wave device including: a subject beam irradiator that irradiates the inside of a subject with an ultrasonic beam or laser beam to cause an acoustic wave to be emitted from a tissue of the subject; an insertion object that can be inserted into the subject and has a photoacoustic wave generator at a distal end portion; an insertion object laser light source that generates a photoacoustic wave from the photoacoustic wave generator by irradiating the photoacoustic wave generator of the insertion object with laser beam; and a reception signal generator that receives the acoustic wave emitted from the tissue of the subject to generate a tomographic image generating reception signal, and receives the photoacoustic wave from the photoacoustic wave generator to generate an insertion object image generating reception signal; a tomographic image signal generator that generates a tomographic image signal that represents a tomographic image of the subject from the tomographic image generating reception signal; an insertion object image signal generator that generates an insertion object image signal that represents an image of the distal end portion of the insertion object from the insertion object image generating reception signal; an insertion object display image signal generator that generates an insertion object display image signal having a center at a peak position where a signal strength of the insertion object image signal becomes a peak value, having a maximum width corresponding to a predetermined reference signal width, and having a signal strength corresponding to the peak value at the center; and a display, wherein the acoustic wave device superimposes the tomographic image of the subject and the image of the distal end portion of the insertion object to be displayed on the display on the basis of the tomographic image signal and the insertion object display image signal.

(Appendix 2) The acoustic wave device according to Appendix 1, wherein the insertion object display image signal generator generates the insertion object display image signal having a center at the peak position, having a maximum value corresponding to the reference signal width, and having a signal strength corresponding to the peak value in an entire portion thereof.

(Appendix 3) The acoustic wave device according to Appendix 2, wherein the insertion object display image signal generator generates a center marker that represents the peak position of the insertion object display image signal, and superimposes the center marker on an image of a distal end portion of the insertion object to be displayed on the display.

(Appendix 4) The acoustic wave device according to Appendix 2 or 3, further including: a first signal width detector that detects a first signal width of the insertion object image signal having a signal strength of a predetermined ratio with respect to the peak value; and an image highlighting unit that highlights and displays the image of the distal end portion of the insertion object.

(Appendix 5) The acoustic wave device according to Appendix 1, wherein the image highlighting unit superimposes an outline of a region having a center at the peak position and having the first signal width on the image of the distal end portion of the insertion object to be displayed on the display.

(Appendix 6) The acoustic wave device according to Appendix 5, wherein the image highlighting unit displays an outer peripheral portion of the image of the distal end portion of the insertion object in different colors on the display between a case where the first signal width is larger than the reference signal width and a case where the first signal width is smaller than the reference signal width.

(Appendix 7) The acoustic wave device according to any one of Appendixes 4 to 6, wherein the image of the distal end portion of the insertion object is displayed in different colors on the display between a case where the first signal width is larger than the reference signal width and a case where the first signal width is smaller than the reference signal width.

(Appendix 8) The acoustic wave device according to any one of Appendixes 2 to 7, further including: an operating unit through which a user performs an input operation; and a reference signal width setting unit that sets the reference signal width, wherein the reference signal width setting unit sets a value set by the user through the operating unit as the reference signal width.

(Appendix 9) The acoustic wave device according to any one of Appendixes 2 to 7, further including: a reference signal width setting unit that sets the reference signal width; and a distal end diameter recording unit that records a diameter of the distal end portion of the insertion object, wherein the reference signal width setting unit calculates a converted value obtained by multiplying the diameter of the distal end portion of the insertion object recorded in the distal end diameter recording unit by a predetermined coefficient, and sets the converted value as the reference signal width.

(Appendix 10) The acoustic wave device according to any one of Appendixes 2 to 9, wherein the subject beam irradiator irradiates the inside of the subject with an ultrasonic beam to cause an ultrasonic echo to be emitted from the tissue of the subject, and wherein the reception signal generator receives the ultrasonic echo from the tissue of the subject to generate the tomographic image generating signal.

(Appendix 11) The acoustic wave device according to any one of Appendixes 2 to 9, wherein the subject beam irradiator irradiates the inside of the subject with laser beam to cause a photoacoustic wave to be emitted from the tissue of the subject, and wherein the reception signal generator receives the photoacoustic wave from the tissue of the subject to generate the tomographic image generating reception signal.

(Appendix 12) An acoustic wave device including a probe that irradiates the inside of a subject with an ultrasonic beam or laser beam; an insertion object that can be inserted into the subject and has a photoacoustic wave generator at a distal end portion; an insertion object laser light source that generates a photoacoustic wave from the photoacoustic wave generator by irradiating the photoacoustic wave generator of the insertion object with laser beam; and a processor that receives an acoustic wave emitted from a tissue of the subject by irradiating the inside of the subject with the ultrasonic beam or the laser beam from the subject beam irradiator to generate a tomographic image generating reception signal and receives a photoacoustic wave from the photoacoustic wave generator to generate an insertion object image generating reception signal, and a display, wherein the processor generates a tomographic image signal representing a tomographic image of the subject from the tomographic image generating reception signal, generates an insertion object image signal representing an image of the distal end portion of the insertion object from the insertion object image generating reception signal, generates an inserted object display image signal having a center at a peak position where a signal strength of the insertion object image signal has a peak value, having a maximum width corresponding to a predetermined reference signal width, and having a signal strength corresponding to the peak value at the center, and superimposes the tomographic image of the subject and the image of the distal end portion of the insertion object to be displayed on the display on the basis of the tomographic image signal and the insertion object display image signal.

EXPLANATION OF REFERENCES 1, 41, 44: Ultrasonic wave device
2, 47A: Array transducer 3: Transmitter
4: Receiver
5: Data separator
6, 49: Tomographic image signal generator
7: Image superposing unit
8: Display controller
9: Display
10: Insertion object image signal generator
11: First signal width detector
12, 36: Insertion object display image signal generator
13: Insertion object
13A: Cable
13B: Connector
14: Insertion object laser light source
15: Device controller
16: Operating unit
17: Storage
18: Probe
19, 43, 43A, 50: Processor
20: Light guide member
21: Photoacoustic wave generator
22: Laser rod
23: Excitation light source
24, 25: Mirror
26: Q switch
29: Amplifier
30: AD converter
31: Signal processing unit
32: DSC
33: Image processing unit
37: Insertion object display image signal specifier
38: Image highlighting unit
42, 42A: Reference signal width setting unit
45: Distal end diameter reader
46: Photoacoustic wave device
47: Probe
47B: Subject laser beam irradiator
48: Subject laser light source
A, FE: Distal end portion
B1: Subject beam irradiator
B2: Reception signal generator
C: Outline image signal
CT1, CT2: Outer peripheral portion
DC1, DC2: Display color
E: Signal strength
FL: Thin line
EL: Lower limit signal strength
M: Center marker image signal
P0: Peak position
SA: Insertion object image signal
SB: Insertion object display image signal
T1, T2: Image of distal end portion of insertion object
U: Tomographic image
W1: First signal width
W2: Reference signal width
W3: Signal width

What is claimed is:

1. An acoustic wave device comprising:
an insertion object that is capable of being inserted into a subject and has a photoacoustic wave generator at a distal end portion;
an insertion object laser light source that generates a photoacoustic wave from the photoacoustic wave generator by irradiating the photoacoustic wave generator of the insertion object with laser beam;
an array transducer that irradiates an inside of the subject with an ultrasonic beam or laser beam, that receives an acoustic wave emitted from a tissue of the subject by irradiating the inside of the subject with the ultrasonic beam or the laser beam irradiated from the array transducer and outputs a tomographic image generating reception signal, and that receives the photoacoustic wave from the photoacoustic wave generator and outputs an insertion object image generating reception signal;
a processor that is configured to receive the tomographic image generating reception signal and the insertion object image generating reception signal; and
a display,
wherein the processor is configured to
generate a tomographic image signal representing a tomographic image of the subject from the tomographic image generating reception signal,
generate an insertion object image signal representing an image of the distal end portion of the insertion object from the insertion object image generating reception signal,
generate an insertion object display image signal having a center at a peak position where a signal strength of the insertion object image signal has a peak value, having a maximum width corresponding to a predetermined reference signal width, and having a signal strength corresponding to the peak value at the center, the insertion object display image signal having the predetermined reference signal width by changing only the insertion object image signal of the tomographic image and the insertion object image signal while a signal width of the insertion object image signal having a signal strength of a predetermined ratio to the peak value of the insertion object image signal is not equal to the predetermined reference signal width, and
superimpose the tomographic image of the subject and the image of the distal end portion of the insertion object to be displayed on the display on the basis of the tomographic image signal and the insertion object display image signal, the image of the distal end portion of the insertion object having a display width corresponding to the predetermined reference signal width.

2. The acoustic wave device according to claim 1, wherein the processor is further configured to
detect a first signal width of the insertion object image signal having a signal strength of a predetermined ratio to the peak value, and
generate, in a case where the first signal width is larger than the reference signal width, an insertion object display image signal formed by a portion ranging from the center to the reference signal width in the insertion object image signal, and generate, in a case where the first signal width is smaller than the reference signal width, an insertion object display image signal having a signal strength greater than a predetermined lower limit signal strength in an entire portion thereof, from the insertion object image signal.

3. The acoustic wave device according to claim 2, wherein the processor is further configured to generate, in a case where the first signal width is smaller than the reference signal width, the insertion object display image signal obtained by increasing a signal strength of a portion including the signal strength smaller than the lower limit signal strength, in the insertion object image signal, up to the lower limit signal strength.

4. The acoustic wave device according to claim 3, wherein the processor is further configured to highlight the image of the distal end portion of the insertion object to be displayed on the display.

5. The acoustic wave device according to claim 4, wherein the processor is further configured to superimpose an outline of a region having a center at the peak position and having the first signal width on the image of the distal end portion of the insertion object to be displayed on the display.

6. The acoustic wave device according to claim 4, wherein the processor is further configured to display an outer peripheral portion of the image of the distal end portion of the insertion object in different colors on the display between a case where the first signal width is larger than the reference signal width and a case where the first signal width is smaller than the reference signal width.

7. The acoustic wave device according to claim 2, wherein the processor is further configured to generate, in a case where the first signal width is smaller than the reference signal width, the insertion object display image signal obtained by enlarging a signal width of a portion including a signal strength larger than the lower limit signal strength, in the insertion object image signal, up to the reference signal width.

8. The acoustic wave device according to claim 7, wherein the processor is further configured to highlight the image of the distal end portion of the insertion object to be displayed on the display.

9. The acoustic wave device according to claim 8, wherein the processor is further configured to superimpose an outline of a region having a center at the peak position and having the first signal width on the image of the distal end portion of the insertion object to be displayed on the display.

10. The acoustic wave device according to claim 8, wherein the processor is further configured to display an outer peripheral portion of the image of the distal end portion of the insertion object in different colors on the display between a case where the first signal width is larger than the reference signal width and a case where the first signal width is smaller than the reference signal width.

11. The acoustic wave device according to claim 2, wherein the processor is further configured to highlight the image of the distal end portion of the insertion object to be displayed on the display.

12. The acoustic wave device according to claim 11, wherein the processor is further configured to superimpose an outline of a region having a center at the peak position and having the first signal width on the image of the distal end portion of the insertion object to be displayed on the display.

13. The acoustic wave device according to claim 12, wherein the processor is further configured to display an outer peripheral portion of the image of the distal end portion of the insertion object in different colors on the display between a case where the first signal width is larger than the reference signal width and a case where the first signal width is smaller than the reference signal width.

14. The acoustic wave device according to claim 11, wherein the processor is further configured to display an outer peripheral portion of the image of the distal end portion of the insertion object in different colors on the display between a case where the first signal width is larger than the reference signal width and a case where the first signal width is smaller than the reference signal width.

15. The acoustic wave device according to claim 11, wherein the processor is further configured to display the image of the distal end portion of the insertion object in different colors on the display between a case where the first signal width is larger than the reference signal width and a case where the first signal width is smaller than the reference signal width.

16. The acoustic wave device according to claim 1, further comprising:
an interface through which a user performs an input operation, wherein
the processor is further configured to
set the reference signal width, and
set a value set by the user through the interface as the reference signal width.

17. The acoustic wave device according to claim 1, further comprising:
an identifier that records a diameter of the distal end portion of the insertion object, wherein
the processor is further configured to
set the reference signal width, and
calculate a converted value obtained by multiplying the diameter of the distal end portion of the insertion object recorded in the identifier by a predetermined coefficient, and set the converted value as the reference signal width.

18. The acoustic wave device according to claim 1, wherein
the array transducer irradiates the inside of the subject with the ultrasonic beam to cause an ultrasonic echo to be emitted from the tissue of the subject, and
the processor is further configured to receive the ultrasonic echo from the tissue of the subject to generate the tomographic image generating reception signal.

19. The acoustic wave device according to claim 1, wherein
the insertion object laser light source irradiates the inside of the subject with laser beam to cause the photoacoustic wave to be emitted from the tissue of the subject, and
the processor is further configured to receive the photoacoustic wave from the tissue of the subject to generate the tomographic image generating reception signal.

20. A control method of an acoustic wave device, the method comprising:
receiving an acoustic wave emitted from a tissue of a subject by irradiating an inside of the subject with an ultrasonic beam or laser beam to generate a tomographic image generating reception signal;
irradiating a photoacoustic wave generator of an insertion object with the laser beam, the insertion object being able to be inserted into the subject and having the photoacoustic wave generator at a distal end portion;
receiving a photoacoustic wave from the photoacoustic wave generator to generate an insertion object image generating reception signal;

generating an insertion object image signal representing an image of the distal end portion of the insertion object from the insertion object image generating reception signal;

generating a tomographic image signal representing a tomographic image of the subject from the tomographic image generating reception signal;

generating an insertion object display image signal having a center at a peak position where a signal strength of the insertion object image signal has a peak value, having a maximum width corresponding to a predetermined reference signal width, and having a signal strength corresponding to the peak value at the center, the insertion object display image signal having the predetermined reference signal width by changing only the insertion object image signal of the tomographic image and the insertion object image signal while a signal width of the insertion object image signal having a signal strength of a predetermined ratio to the peak value of the insertion object image signal is not equal to the predetermined reference signal width; and superimposing the tomographic image of the subject and the image of the distal end portion of the insertion object to be displayed on a display on the basis of the tomographic image signal and the insertion object display image signal, the image of the distal end portion of the insertion object having a display width corresponding to the predetermined reference signal width.

* * * * *